(12) United States Patent
Tuyl et al.

(10) Patent No.: US 11,404,156 B2
(45) Date of Patent: Aug. 2, 2022

(54) METHODS FOR MANAGING BEHAVIORAL TREATMENT THERAPY AND DEVICES THEREOF

(71) Applicant: Catalight Foundation, Walnut Creek, CA (US)

(72) Inventors: Robert van Tuyl, Pleasanton, CA (US); Susan Armiger, Walnut Creek, CA (US); Doreen Samelson, Stockton, CA (US); Nhan T. Nguyen, Lafayette, CA (US)

(73) Assignee: CATALIGHT FOUNDATION, Walnut Creek, CA (US)

( * ) Notice: Subject to any disclaimer, the term of this patent is extended or adjusted under 35 U.S.C. 154(b) by 131 days.

(21) Appl. No.: 16/112,566

(22) Filed: Aug. 24, 2018

(65) Prior Publication Data

US 2019/0066834 A1 Feb. 28, 2019

Related U.S. Application Data

(60) Provisional application No. 62/550,501, filed on Aug. 25, 2017.

(51) Int. Cl.
*G16H 20/70* (2018.01)
*A61M 21/02* (2006.01)
(Continued)

(52) U.S. Cl.
CPC .......... *G16H 20/70* (2018.01); *A61B 5/0036* (2018.08); *A61B 5/02055* (2013.01);
(Continued)

(58) Field of Classification Search
CPC .... A61M 21/00–02; A61M 2205/3303; A61M 2205/3553; G16H 20/70;
(Continued)

(56) References Cited

U.S. PATENT DOCUMENTS

| | | | |
|---|---|---|---|
| 2016/0000640 A1* | 1/2016 | Lai | A61H 9/0078 601/149 |
| 2016/0019693 A1 | 1/2016 | Silbersweig et al. | |

(Continued)

OTHER PUBLICATIONS

International Search Report for corresponding PCT Application No. PCT/US18/48024 dated Nov. 2, 2018.
(Continued)

*Primary Examiner* — Thaddeus B Cox
(74) *Attorney, Agent, or Firm* — Troutman Pepper Hamilton Sanders LLP (Rochester)

(57) ABSTRACT

A method, non-transitory computer readable medium and apparatus that manages behavioral treatment therapy includes generating a treatment plan comprising therapeutic techniques that is transmitted to at least one of a client at a client device or a practitioner at a practitioner device associated with the client. Analytic data may be obtained regarding execution of at least one of the therapeutic techniques and at least one of biomarker data from at least one biomarker sensor coupled to the client or environmental data from at least one environmental characteristic sensor during execution of the therapeutic technique. One or more of the therapeutic techniques are adjusted based on the analytic data and the at least one of the biomarker data or the environmental data. The adjusted one or more of the therapeutic techniques are transmitted to at least one of the client device or the practitioner device.

30 Claims, 7 Drawing Sheets

(51) Int. Cl.
*A61B 5/16* (2006.01)
*G16H 40/67* (2018.01)
*G16H 80/00* (2018.01)
*A61M 21/00* (2006.01)
*A61B 5/0205* (2006.01)
*A61B 5/00* (2006.01)
*G16H 50/20* (2018.01)
*G16H 10/60* (2018.01)
*A61B 5/11* (2006.01)
*A61B 5/024* (2006.01)
*A61B 5/08* (2006.01)
*A61B 5/01* (2006.01)

(52) U.S. Cl.
CPC ............ *A61B 5/165* (2013.01); *A61B 5/4836* (2013.01); *A61M 21/02* (2013.01); *G16H 10/60* (2018.01); *G16H 40/67* (2018.01); *G16H 50/20* (2018.01); *G16H 80/00* (2018.01); *A61B 5/0022* (2013.01); *A61B 5/0077* (2013.01); *A61B 5/01* (2013.01); *A61B 5/024* (2013.01); *A61B 5/0816* (2013.01); *A61B 5/1123* (2013.01); *A61B 5/486* (2013.01); *A61B 2560/0252* (2013.01); *A61B 2560/0257* (2013.01); *A61M 2021/005* (2013.01); *A61M 2021/0022* (2013.01); *A61M 2205/3303* (2013.01); *A61M 2205/3375* (2013.01); *A61M 2205/3553* (2013.01); *A61M 2205/502* (2013.01); *A61M 2205/52* (2013.01)

(58) Field of Classification Search
CPC ........ G16H 40/67; G16H 80/00; A61B 5/165; A61B 5/4836; A61B 5/486
See application file for complete search history.

(56) References Cited

U.S. PATENT DOCUMENTS

| | | | |
|---|---|---|---|
| 2016/0019813 A1* | 1/2016 | Mullen | G16H 40/63 434/236 |
| 2016/0140320 A1 | 5/2016 | Moturu et al. | |
| 2017/0039336 A1* | 2/2017 | Bitran | G16H 20/70 |
| 2017/0326330 A1* | 11/2017 | Bulaj | A61M 21/00 |
| 2018/0303412 A1* | 10/2018 | Moore | G16H 50/20 |

OTHER PUBLICATIONS

European Search Report for European Application No. 18847922.4, dated Oct. 18, 2021.
Examination Report for Great Britain Application No. GB2011900.4, dated Nov. 30, 2021.

* cited by examiner

METHODS FOR MANAGING BEHAVIORAL TREATMENT THERAPY AND DEVICES THEREOF

This application claims the benefit of U.S. Provisional Application No. 62/550,501, filed Aug. 25, 2017, which is hereby incorporated by reference in its entirety.

RELATED APPLICATION

This application is related to U.S. Provisional Patent Application Ser. No. 62/461,184 filed Feb. 20, 2017, which is hereby incorporated by reference in its entirety.

FIELD

This technology relates to methods for managing behavioral treatment therapy that is intended to be used by clients, caregivers, and practitioners to more effectively support continuous, interactive, and ongoing adaptive home and community care in the healthcare industry and devices thereof.

BACKGROUND

Clients with Autism Spectrum Disorder (ASD) benefit from therapy programs that are directed to reducing the associated deficits and behaviors, thereby increasing the quality of life and functional independence of affected individuals. One characteristic of such treatment programs is that they require periodic therapy sessions with a practitioner, also known as a behavioral interventionist (BI), over a long period of time with the need for periodic assessment and adjustments based on the individual's situation.

Most legacy solutions simply consist of manual software implementations that involve paper data collection forms and reports, where a practitioner uses a copy of a template form that represents a treatment plan that was selected by a program supervisor from a set of pre-defined treatment plans, based on the client's diagnosis. Very few, if any, software based solutions, have been developed to manage the dynamic and long term nature these behavioral therapy programs require to have success.

Unfortunately, these legacy solutions have a number of shortcomings and technological issues. These shortcomings and technological issues include that these prior legacy solutions are cumbersome, rely on rigid and relatively fixed templates, and may be inconsistently applied to similarly situated clients because of an unintended correlation or other error. Additionally, these prior legacy solutions have lacked the technological ability to flexibly adapt to the ongoing and changing therapy needs and circumstances of a current client negatively impacting progress with ongoing therapy. For example, these prior legacy solutions have lacked the technological ability to both identify and utilize other significant related data impacting behavioral treatment plans. Additionally, these prior legacy solutions have failed to provide technological solutions to effect any corrective change on, for example, devices worn by the client and/or in the environment of the client to change the course of an execution of a therapeutic technique. Further, these prior legacy solutions have lacked the technological capability to accurately identify which other client or clients might be related to the current behavioral treatment plan for a current client or the ability to effectively analyze and extract relevant additions or changes to provide more effective and adaptive ongoing behavioral treatment plans. Even further, these prior legacy solutions have failed to effectively integrate and manage the interaction and assistance of related caregivers and behavioral interventionists with the current client or to provide any effective technological solutions for enhancing and coordinating any such interaction to facilitate better treatment and necessary interventions.

SUMMARY

A method for managing behavioral treatment therapy may include generating, by a treatment plan management computing device, a treatment plan comprising a plurality of therapeutic techniques that is transmitted to at least one of a client at a client device or a practitioner at a practitioner device associated with the client. Analytic data may be obtained, by the treatment plan management computing device, regarding execution of at least one of the therapeutic techniques from at least one of the client device or the practitioner device and at least one of biomarker data from at least one biomarker sensor coupled to the client or environmental data from at least one environmental characteristic sensor during execution of the at least one of the therapeutic techniques. One or more of the plurality of therapeutic techniques of the treatment plan are adjusted, by the treatment plan management computing device, based on the analytic data and the at least one of the biomarker data or the environmental data. The adjusted one or more of the plurality of therapeutic techniques of the treatment plan are transmitted, by the treatment management computing device, to at least one of the client device or the practitioner device.

A treatment plan management computing apparatus with a memory coupled to a processor which is configured to be capable of executing programmed instructions comprising and stored in the memory to generate a treatment plan comprising a plurality of therapeutic techniques that is transmitted to at least one of a client at a client device or a practitioner at a practitioner device associated with the client. Analytic data may be obtained regarding execution of at least one of the therapeutic techniques from at least one of the client device or the practitioner device and at least one of biomarker data from at least one biomarker sensor coupled to the client or environmental data from at least one environmental characteristic sensor during execution of the at least one of the therapeutic techniques. One or more of the plurality of therapeutic techniques of the treatment plan are adjusted based on the analytic data and the at least one of the biomarker data or the environmental data. The adjusted one or more of the plurality of therapeutic techniques of the treatment plan are transmitted to at least one of the client device or the practitioner device.

A non-transitory computer readable medium having stored thereon instructions comprising executable code which when executed by one or more processors, causes the one or more processors to generate a treatment plan comprising a plurality of therapeutic techniques that is transmitted to at least one of a client at a client device or a practitioner at a practitioner device associated with the client. Analytic data may be obtained regarding execution of at least one of the therapeutic techniques from at least one of the client device or the practitioner device and at least one of biomarker data from at least one biomarker sensor coupled to the client or environmental data from at least one environmental characteristic sensor during execution of the at least one of the therapeutic techniques. One or more of the plurality of therapeutic techniques of the treatment plan are adjusted based on the analytic data and the at least one of the biomarker data or the environmental data. The adjusted one or more of the plurality of therapeutic techniques of the treatment plan are transmitted to at least one of the client device or the practitioner device.

This technology provides a number of advantages including providing methods, non-transitory computer readable medium and apparatuses that manage behavioral treatment therapy that is intended to be used by clients, caregivers, and practitioners to more effectively support continuous, interactive and ongoing adaptive home and community care in the healthcare industry. This technology also substantially enhances the quality of care through a continuous real time management and monitoring of behavioral treatment plans utilizing inputs from multiple members of a caregiving team as well as various sensors and managing actuator controlled treatment and/or environmental characteristic devices. Additionally, this technology enables dynamic adjustment of behavioral treatment plans in order to provide customized individual treatment delivery and necessary interventions in real time. Further, this technology provides a mechanism that enables behavioral treatment plans to evolve for long term use based on needs and results from a particular client and/or additional feedback gathered and processed by artificial intelligence located at the edge from other behavioral treatment plan use cases. This technology also effectively integrates multiple types of caregivers and practitioners as well as the monitoring and control over a variety of internet-of-things solutions, such as different sensors and devices used by or in the surrounding area of the client to increase the chances of success with particular therapeutic techniques. Further, this technology enables the cross-correlation of behavioral treatment plans for clients along multiple levels to enable more effective integration of past feedback data when customizing behavioral treatment plans.

DETAILED DESCRIPTION

Figure 1:
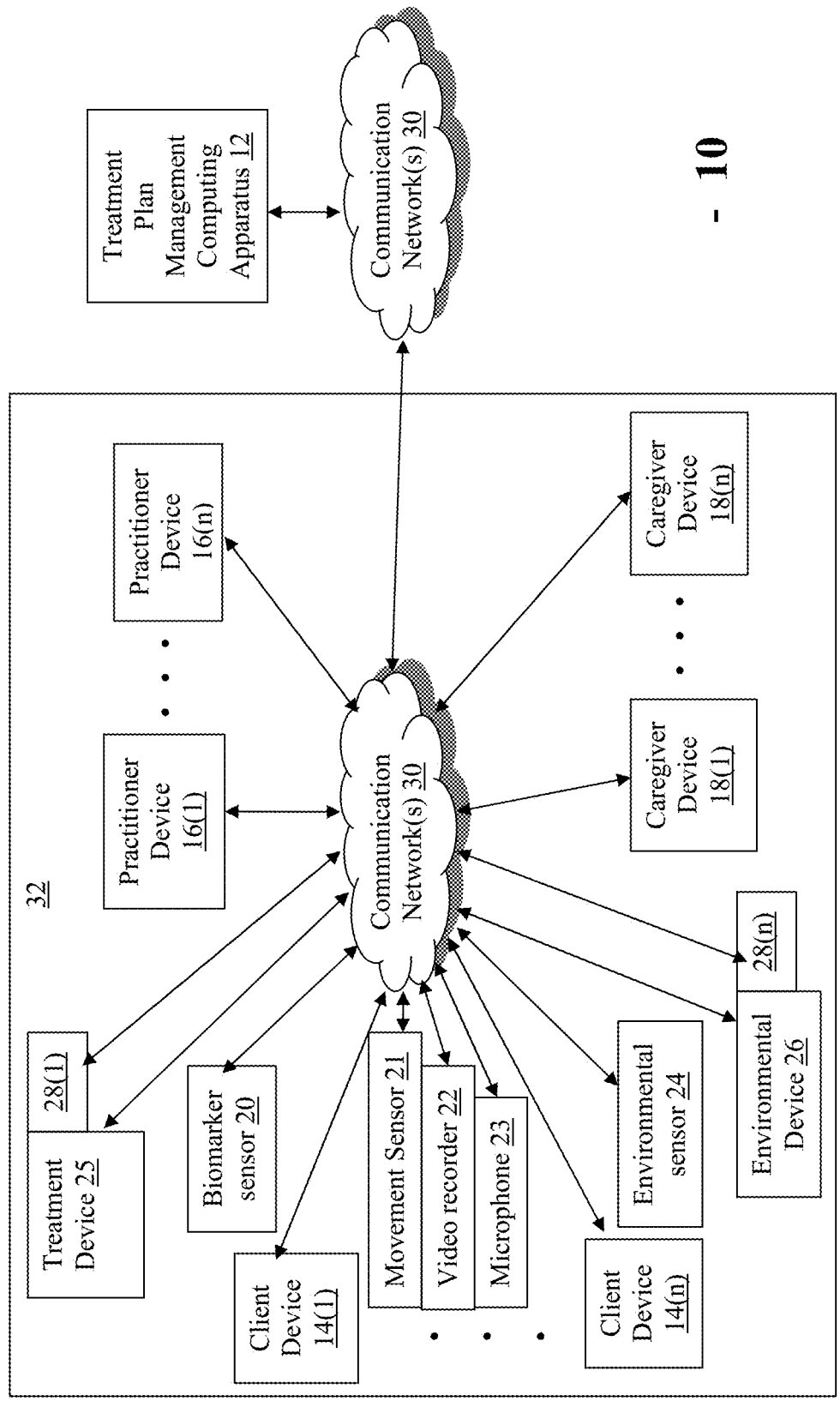
FIG. 1 is a diagram of an exemplary living environment with a plurality of devices, a plurality of caregiver devices, and a plurality of practitioner devices coupled to an example of a treatment management computing apparatus.
Figure 2A:
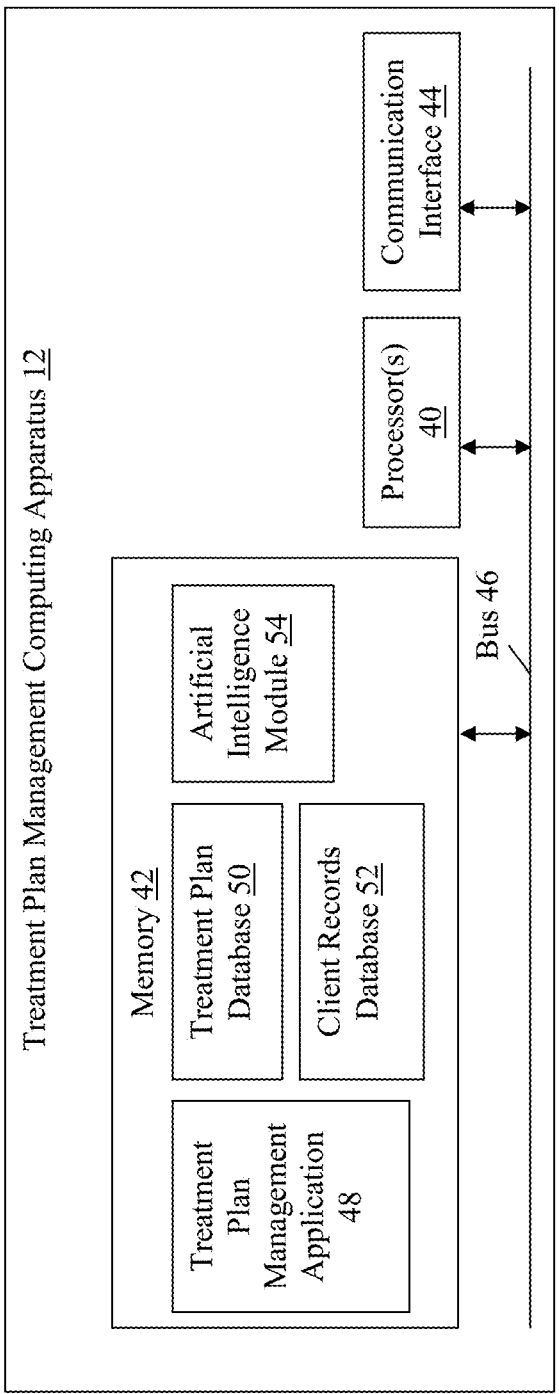
FIG. 2A is a diagram of an example of the treatment plan management computing apparatus with an example of a treatment plan management application.
Figure 2B:
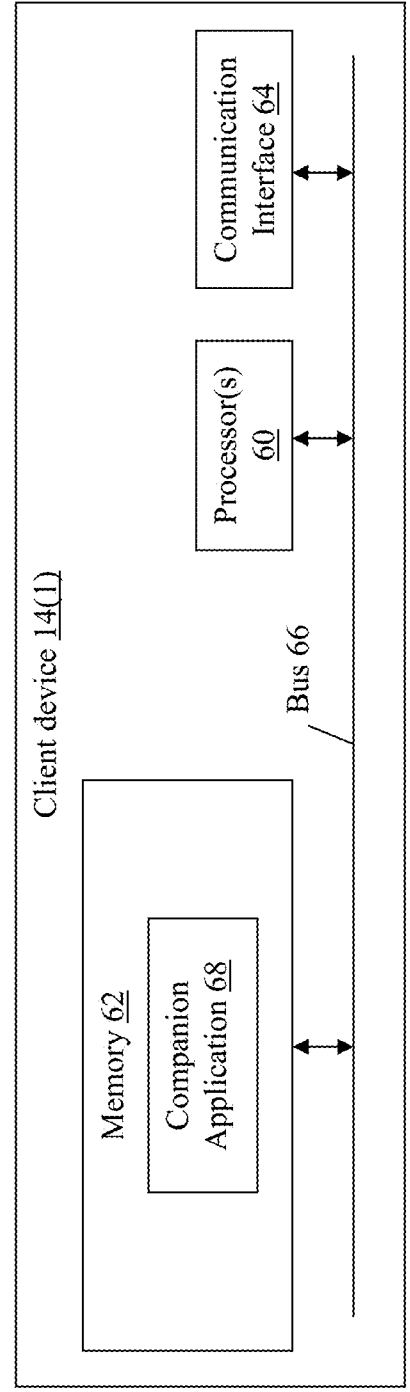
FIG. 2B is a diagram of an example of one of the client devices with an example of a companion application.

An exemplary environment 10 with an example of a treatment plan management computing apparatus 12 illustrated in FIGS. 1-2B. In this example, the environment 10 includes the treatment plan management computing apparatus 12, a plurality of client devices 14(*l*)-14(*n*), a plurality of practitioner devices 16(1)-16(*n*), a plurality of caregiver devices 18(1)-18(*n*), a biomarker sensor 20, a movement sensor 21, a video recorder 22, a microphone 23, an environmental characteristic sensor 24, a treatment device 25, an environmental characteristic device 26, and actuators 28(1)-28(*n*), although the environment may have other types and/or numbers of other systems, devices, components, and/or other elements in other arrangements. Additionally, in this example the plurality of client devices 14(1)-14(*n*), the plurality of practitioner devices 16(1)-16(*n*), the plurality of caregiver devices 18(1)-18(*n*), the biomarker sensor 20, the movement sensor 21, the video recorder 22, the microphone 23, the environmental characteristic sensor 24, the treatment device 25, the environmental characteristic device 26, and the actuators 28(1)-28(*n*) are illustrated within residential community building 32, although one or more may be in other and/or different accommodations and/or environments. Further, this environment 10 may include other network devices, such as one or more routers and/or switches, for example, which are well known in the art and thus will not be described herein. This technology provides a number of advantages including methods, non-transitory computer readable media, and apparatuses that manage behavioral treatment therapy that is intended to be used by clients, caregivers, and practitioners to more effectively support continuous, interactive and ongoing adaptive home and community care in the healthcare industry.

Referring more specifically to FIGS. 1 and 2A, the treatment plan management computing apparatus 12 may perform any number of functions including by way of example for managing behavioral treatment therapy as illustrated and described by way of the examples herein, although this technology may be used in a variety of other areas, such as treatment plans for managing health, fitness, and/or physical therapy. The treatment plan management computing apparatus 12 may include a processor(s) 40, a memory 42, and/or a communication interface 44, which are coupled together by a bus or other communication link 46, although the treatment plan management computing apparatus 12 can include other types and/or numbers of elements in other configurations.

The processor(s) 40 of the treatment plan management computing apparatus 12 may execute programmed instructions stored in the memory of the treatment plan management computing apparatus 12 for the any number of the functions as illustrated by way of the examples herein. The processor(s) 40 of the treatment plan management computing apparatus 12 may include one or more CPUs or general purpose processors with one or more processing cores, for example, although other types of processor(s) also can be used.

The memory 42 of the treatment plan management computing apparatus 12 stores these programmed instructions for one or more aspects of the present technology as described and illustrated herein, although some or all of the programmed instructions could be stored elsewhere. A variety of different types of memory storage devices, such as random access memory (RAM), read only memory (ROM), hard disk, solid state drives, flash memory, or other computer readable medium which is read from and written to by a magnetic, optical, or other reading and writing system that is coupled to the processor(s) 40, can be used for the memory 42.

Accordingly, the memory 42 of the treatment plan management computing apparatus 12 can store one or more applications that can include computer executable instructions that, when executed by the treatment plan management computing apparatus 12, cause the treatment plan management computing apparatus 12 to perform actions, such as to transmit, receive, or otherwise process messages, for example, and to perform other actions described and illustrated by way of the examples below with reference to FIGS. 3-7. The application(s) can be implemented as modules or components of other applications. Further, the application(s) can be implemented as operating system extensions, module, plugins, or the like.

Even further, the application(s) may be operative in a cloud-based computing environment. The application(s) can be executed within or as virtual machine(s) or virtual server(s) that may be managed in a cloud-based computing environment. Also, the application(s), and even the treatment plan management computing apparatus 12 itself, may be located in virtual server(s) running in a cloud-based computing environment rather than being tied to one or more specific physical network computing devices. Also, the application(s) may be running in one or more virtual machines (VMs) executing on the treatment plan management computing apparatus 12. Additionally, in one or more examples of this technology, virtual machine(s) running on the treatment plan management computing apparatus 12 may be managed or supervised by a hypervisor.

In this particular example, the memory 42 of the treatment plan management computing apparatus 12 includes a treatment plan management application (TMPA) 48, a treatment plan database 50, a client records database, and an artificial intelligence module 54 although the memory can include other policies, modules, programmed instructions, databases, and/or applications, for example. The treatment plan management application 48 may include programmed instructions for managing behavioral treatment therapy as illustrated and described by way of the examples herein, although the application may include other types and/or numbers of other operations and/or functions. Additionally, the treatment plan management application 48 may enable: creation of electronic treatment plans based on stored models of templates and current assessments of clients based on stored evaluation data; management of ongoing treatment and adjustments; changes, edits and updates to therapeutic treatments and/or treatment goals; management of treatment schedules by practitioners and caregivers; provision of current treatment results and other status information; and management of storage and analysis of client data, although the treatment plan management application 48 may again perform other types and/or numbers of other functions and operations The treatment plan database 50 may include comprise electronic templates of different behavioral treatment plan each comprising a plurality of therapeutic techniques for different types of conditions, although other types and/or amounts of information may be stored. The client records database 52 may comprise stored client treatment data that may be utilized by the artificial intelligence module 54 for analysis to adjust or otherwise modify behavioral treatment plans each comprising a plurality of therapeutic techniques based on past treatment histories, although other types and/or amounts of client data may be stored. The artificial intelligence module 54 may comprise machine learning instructions as illustrated and described by way of the examples herein to analyze and adjust or otherwise modify behavioral treatment plan each comprising a plurality of therapeutic techniques, although other types and/or numbers of artificial intelligence modules may be used.

The communication interface 44 of the treatment plan management computing apparatus 12 operatively couples and communicates with the plurality of client devices 14(1)-14(n), the plurality of practitioner devices 16(1)-16(n), the plurality of caregiver devices 18(1)-18(n), the biomarker sensor 20, the movement sensor 21, the video recorder 22, the microphone 23, the environmental characteristic sensor 24, the treatment device 25, the environmental characteristic device 26, and/or the actuators 28(1)-28(n) which are all coupled together by the communication network(s) 30, although other types and/or numbers of communication networks or systems with other types and/or numbers of connections and/or configurations to other devices and/or elements can also be used.

By way of example only, the communication network(s) 30 can include local area network(s) (LAN(s)), wide area network(s) (WAN(s)), or personal area networks (PAN(s)) such as Bluetooth, and can use TCP/IP over Ethernet and industry-standard protocols, although other types and/or numbers of protocols and/or communication networks can be used. The communication network(s) 30 in this example can employ any suitable interface mechanisms and network communication technologies including, for example, teletraffic in any suitable form (e.g., voice, modem, and the like), Public Switched Telephone Network (PSTNs), Ethernet-based Packet Data Networks (PDNs), combinations thereof, and the like. The communication network(s) 30 can also include direct connection(s) (e.g., for when a device illustrated in FIG. 1, such as the treatment plan management computing apparatus 12, one or more of the client devices 14(1)-14(n), one or more of the practitioner devices 16(1)-16(n), or one or more caregiver devices 18(1)-18(n) operate as virtual instances on the same physical machine).

While the treatment plan management computing apparatus 12 is illustrated in this example as including a single device, the treatment plan management computing apparatus 12 in other examples can include a plurality of devices or blades each having one or more processors (each processor with one or more processing cores) that implement one or more steps of this technology. In these examples, one or more of the devices can have a dedicated communication interface or memory. Alternatively, one or more of the devices can utilize the memory, communication interface, or other hardware or software components of one or more other devices included in the treatment plan management computing apparatus 12.

Additionally, one or more of the devices that together comprise the treatment plan management computing apparatus 12 in other examples can be standalone devices or integrated with one or more other devices or apparatuses, such as one of the client devices 14(1)-14(n), practitioner devices 16(1)-16(n), or one of the caregiver devices 18(1)-18(n) by way of example only. Moreover, one or more of these devices that comprise the treatment plan management computing apparatus 12 in these examples can be in a same or a different communication network including one or more public, private, or cloud networks, for example.

The client devices 14(1)-14(n) in this example include any type of computing device, such as mobile computing devices, desktop computing devices, laptop computing devices, tablet computing devices, virtual machines (including cloud-based computers), or the like. In this example, each of the client devices 14(1)-14(n) is associated with a different client who is receiving ongoing behavioral therapy treatment, although one or more of the client devices 14(1)-14(n) may be associated with other individuals, such as a caregiver of the client by way of another example only. Each of the client devices 14(1)-14(n) in this example includes a processor, a memory, and a communication interface, which are coupled together by a bus or other communication link, although other numbers and/or types of network devices could be used.

The client devices 14(1)-14(n) may run interface applications, such as standard Web browsers or standalone client applications, and may interact with the treatment plan management computing apparatus 12, one or more of the practitioner devices 16(1)-16(n), the caregiver devices 18(1)-18(n), the biomarker sensor 20, the movement sensor 21, the video recorder 22, the microphone 23, the environmental characteristic sensor 24, the treatment device 25, the environmental characteristic device 26, and/or the actuators 28(1)-28(n) via the communication network(s) 30. The client devices 14(1)-14(n) may further include a display device, such as a display screen or touchscreen, and/or an input device, such as a keyboard for example.

Referring more specifically to FIGS. 1 and 2B, one of the client devices 14(1) is illustrated in greater detail. In this particular example, the other client devices 14(2)-14(n) are identical in structure and operation to client device 14(1), although in other examples other types of client devices with other structures and/or other manners of operation may be used.

The processor(s) 60 of the client device 14(1) may execute programmed instructions stored in the memory of the client device 14(1) for the any number of the functions and other operations as illustrated by way of the examples herein. The processor(s) 60 of the client device 14(1) may include one or more CPUs or general purpose processors with one or more processing cores, for example, although other types of processor(s) also can be used.

The memory 62 of the client device 14(1) stores these programmed instructions for one or more aspects of the present technology as described and illustrated herein, although some or all of the programmed instructions could be stored elsewhere. A variety of different types of memory storage devices, such as random access memory (RAM), read only memory (ROM), hard disk, solid state drives, flash memory, or other computer readable medium which is read from and written to by a magnetic, optical, or other reading and writing system that is coupled to the processor(s) 40, can be used for the memory 62.

Accordingly, the memory 62 of the client device 14(1) can store one or more applications that can include computer executable instructions that, when executed by the treatment plan management computing apparatus 12, cause the client device 14(1) to perform actions, such as to transmit, receive, or otherwise process messages, for example, and to perform other actions described and illustrated by way of the examples below with reference to FIGS. 3-7. The application(s) can be implemented as modules or components of other applications. Further, the application(s) can be implemented as operating system extensions, module, plugins, or the like.

Even further, the application(s) may be operative in a cloud-based computing environment. The application(s) can be executed within or as virtual machine(s) or virtual server(s) that may be managed in a cloud-based computing environment. Also, the application(s), and even the client device 14(1) itself, may be located in virtual server(s) running in a cloud-based computing environment rather than being tied to one or more specific physical network computing devices. Also, the application(s) may be running in one or more virtual machines (VMs) executing on the treatment plan management computing apparatus 12. Additionally, in one or more examples of this technology, virtual machine(s) running on the client device 14(1) may be managed or supervised by a hypervisor.

In this particular example, the memory 62 of the client device 14(1) includes a companion application (Companion App or CA) 68, although the memory can include other types and/or numbers of other policies, modules, programmed instructions, databases, and/or applications, for example. The companion application 68 may include programmed instructions for managing behavioral treatment therapy as illustrated and described by way of the examples herein, although the application may include other types and/or numbers of other operations and/or functions. By way of example only, the companion application 68 may provide therapeutic techniques, such as games and activities by way of example, for the client associated with one of the client devices 14(1)-14(n) to interact with in order to record inputs and process results of the ability of the client ability to engage with the activities, thus further providing additional analytic data of cognitive and/or behavioral types of responses from the client to a particular therapeutic technique. Additionally, by way of further example the companion application 68 may give the client, caregiver, and/or practitioner the ability to review a current generated behavioral treatment plan, instructions on how to execute a next therapeutic technique of the treatment plan, and an ability to record results of the execution of the treatment plan. By way of a further example, the companion application 68 may enable: coordination of care by a caregiver associated with one of the caregiver devices 18(1)-18(n) to continue execution of a behavioral treatment plan after and/or in between treatment windows from an assigned practitioner associated with one of the practitioner devices 16(1)-16(n); generate automatic updates to each caregiver and practitioner regarding the current status of ongoing therapy; and providing intervention indications and instructions, although again other types and/or number of other functions and/or operations may be performed. Further, by way of example the companion application 68 may include logic or other programmed instructions to collect and forward sensor data with additional metadata, such as event time and/or duration, although other types and/or amounts of metadata may be captured.

Figure 3:
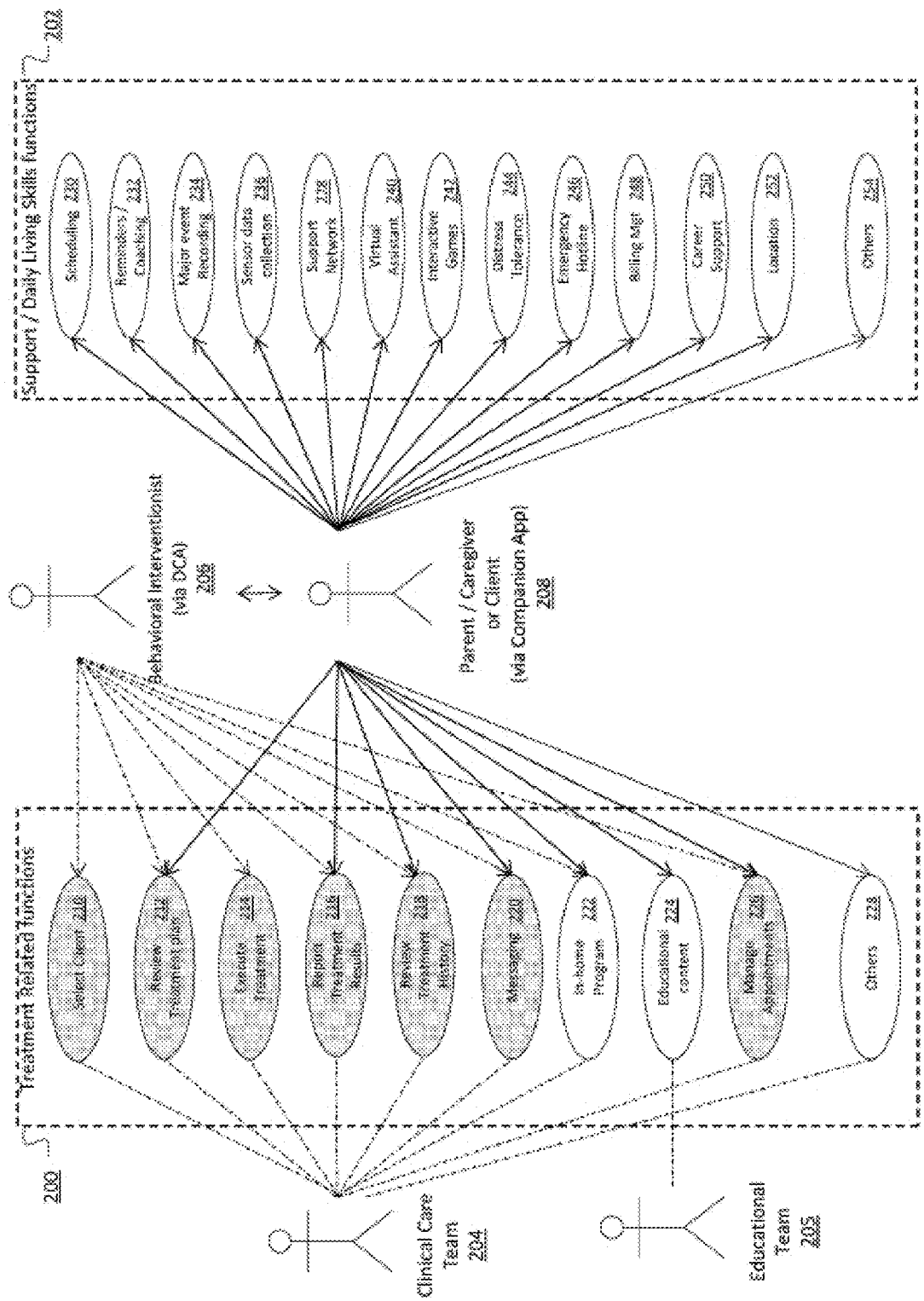
FIG. 3 is a UML use case diagram of an example of functions and other operations of an example of a companion application and exemplary users.

A more detailed example of an example of the companion application 68 is illustrated and described herein with reference to FIG. 3. In this particular example, each of the client devices 14(1)-14(n) as well as each of the practitioner devices 16(1)-16(n) and caregiver devices 18(1)-18(n) may have the companion application 68 downloaded from the treatment plan management computing apparatus 12 for execution of different aspects of this technology including by way of example interaction with the treatment plan management computing apparatus 12 and between one or more of the client devices 14(1)-14(n), the practitioner devices 16(1)-16(n), and/or the caregiver devices 18(1)-18(n) as illustrated and described by way of the examples herein.

The communication interface 44 of the client device 14(1) operatively couples and communicates with the treatment plan management computing apparatus 12, one or more of the other client devices 14(2)-14(n), one or more of the practitioner devices 16(1)-16(n), and/or one or more of the caregiver devices 18(1)-18(n), which are all coupled together by the communication network(s) 30, although other types and/or numbers of communication networks or systems with other types and/or numbers of connections and/or configurations to other devices and/or elements can also be used.

The practitioner devices 16(1)-16(n) in this example include any type of computing device, such as mobile computing devices, desktop computing devices, laptop computing devices, tablet computing devices, virtual machines (including cloud-based computers), or the like. Each of the practitioner devices 16(1)-16(n) in this example includes one or more processors, a memory, and a communication interface, which are coupled together by a bus or other communication link, although other numbers and/or types of network devices could be used. In this example, each of the practitioner devices 16(1)-16(n) is associated with a different behavioral interventionist or other type of practitioner associated with managing the care of one or more clients that are receiving ongoing treatment, although one or more of the practitioner devices 16(1)-16(n) may be associated with other individuals, such as a medical facility by way of another example only. As noted earlier, in this particular example each of the practitioner devices 16(1)-16(n) is executing a copy of the companion application 62 to implement one or more aspects of this technology as illustrated and described by way of the examples herein. The practitioner devices 16(1)-16(n) in this example may interact with the treatment plan management computing apparatus 12, the plurality of client devices 14(1)-14(n), the plurality of caregiver devices 18(1)-18(n), the biomarker sensor 20, the movement sensor 21, the video recorder 22, the microphone 23, the environmental characteristic sensor 24, the treatment device 25, the environmental characteristic device 26, and/or the actuators 28(1)-28(n) via the communication network(s) 30. The practitioner devices 16(1)-16(n) may be hardware or software or may represent a system with multiple servers in a pool, which may include internal or external networks.

Although the practitioner devices 16(1)-16(n) are illustrated as single devices, one or more actions of each of the practitioner devices 16(1)-16(n) may be distributed across one or more distinct network computing devices that together comprise one or more of the practitioner devices 16(1)-16(n). Moreover, the practitioner devices 16(1)-16(n) are not limited to a particular configuration. Thus, the practitioner devices 16(1)-16(n) may contain a plurality of network computing devices that operate using a master/slave approach, whereby one of the network computing devices of the practitioner devices 16(1)-16(n) operate to manage and/or otherwise coordinate operations of the other network computing devices. The practitioner devices 16(1)-16(n) may operate as a plurality of network computing devices within a cluster architecture, a peer-to peer architecture, virtual machines, or within a cloud architecture, for example.

Thus, the technology disclosed herein is not to be construed as being limited to a single environment and other configurations and architectures are also envisaged. For example, one or more of the practitioner devices 16(1)-16(n) can operate within the treatment plan management computing apparatus 12 itself rather than as a stand-alone store server device communicating with the treatment plan management computing apparatus 12 via the communication network(s) 30.

The caregiver devices 18(1)-18(n) in this example include any type of computing device, such as mobile computing devices, desktop computing devices, laptop computing devices, tablet computing devices, virtual machines (including cloud-based computers), or the like. In this example, each of the caregiver devices 18(1)-18(n) is associated with a different caregiver for one of the clients that are receiving ongoing behavioral therapy treatment, such as one or more parents and/or siblings by way of example, although one or more of the caregiver devices 18(1)-18(n) may be associated with other individuals. Each of the caregiver devices 18(1)-18(n) in this example includes a processor, a memory, and a communication interface, which are coupled together by a bus or other communication link, although other numbers and/or types of network devices could be used. As noted earlier, in this particular example each of the caregiver devices 18(1)-18(n) may be executing a copy of the companion application 62 to implement one or more aspects of this technology as illustrated and described by way of the examples herein.

The caregiver devices 18(1)-18(n) may interact with the treatment plan management computing apparatus 12, the plurality of client devices 14(1)-14(n), the plurality of practitioner devices 16(1)-16(n), the biomarker sensor 20, the movement sensor 21, the video recorder 22, the microphone 23, the environmental characteristic sensor 24, the treatment device 25, the environmental characteristic device 26, and/or the actuators 28(1)-28(n) via the communication network(s) 30. The caregiver devices 18(1)-18(n) may further include a display device, such as a display screen or touchscreen, and/or an input device, such as a keyboard for example.

This example of the technology may also include one or more other sensors detachably or otherwise coupled to the client, such as wearable sensors, and/or may include other sensors in the surround area or environment, such as the residential community building 32 in this particular example, where one or more of the plurality of therapeutic techniques are executed. One or more of the sensors may optionally contain logic that only reports sensor data when a corresponding value rise above a predefined threshold obtained or otherwise set in this example from or by the treatment plan management apparatus 12 to minimize unnecessary communications while still providing necessary checks. Additionally readings from multiple sensors may be coordinated combined analysis in order to more accurately detect a state of mind or other condition of the client related to the behavioral treatment plan. Incorporation of different types and utilization of different combinations of these sensors to generate and adjust behavioral treatment plans and/or a plurality of therapeutic techniques as illustrated and described by way of the examples herein is not well understood, routine or conventional in this technology space and provides greater insight to factors impacting success or failure of therapeutic techniques.

In this particular example, the technology includes the biomarker sensor 20, the movement sensor 21, the video recorder 22, the microphone 23, and the environmental characteristic sensor 24 which are each coupled via one or more communication network(s) 30 to the treatment plan management computing apparatus 12. In this example, the biomarker sensor 20 is a sensor or sensors coupled to the client to monitor one or more of heart rate, respiration, body temperature, or anxiety level, although other types and/or numbers of sensors monitoring other aspects may be used. Additionally, in this example the movement sensor 21 comprises a GPS or other movement monitoring device that monitors and tracks a location or other movement(s) of the client, such as other stereotypical or other movements of the client (for example, stimming) that may indicate a state of distress, although other types of movement sensors monitoring other types of movements of the client or parts of the client maybe used. The video recorder 22 is positioned in this example in the residential community building 32 and is used to record video of the client during execution of one or more of the therapeutic techniques, although the video recorder 22 could be in other locations and may record other video related to the client. The microphone 23 is positioned in this example in the residential community building 32 and is used to record audio of the client during execution of one or more of the therapeutic techniques, although the microphone 23 could be in other locations and may record other audio related to the client. The environmental characteristic sensor 25 is positioned in this example in the residential community building 32 and is used to capture environmental characteristics in the environment around the client, such as a temperature reading, a pressure reading, and/or lighting level reading and may also monitor and identify changes in these readings by way of example, during execution of one or more of the therapeutic techniques, although the environmental characteristic sensor 25 could be in other locations and may record other environmental characteristics related to the client.

This example of the technology may also include one or more other devices which are each coupled to an actuator in this example to be managed and controlled by the treatment plan management computing apparatus 12. In this example, the treatment device 25 may comprise a pressure vest that the client may wear and may be controlled by an actuator 28(1) in response to programmed instructions received from the treatment plan management computing apparatus 12, such as to increase or decrease pressure, although treatment plan management computing apparatus 12 may interact with other types of medical support devices that are coupled to the client. Additionally, in this example the environmental characteristic device 26 may comprise a thermostat, humidifier, or lighting device by way of example only that may be controlled by an actuator 28(n) in response to programmed instructions received from the treatment plan management computing apparatus 12, such as to increase or decrease temperature, humidity, or a lighting level, although treatment plan management computing apparatus 12 may interact with other types of environmental characteristic devices that are in a surround area of the client.

Although the exemplary treatment plan management computing apparatus 12, the plurality of client devices 14(1)-14(n), the plurality of practitioner devices 16(1)-16(n), the plurality of caregiver devices 18(1)-18(n), the biomarker sensor 20, the movement sensor 21, the video recorder 22, the microphone 23, the environmental characteristic sensor 24, the treatment device 25, the environmental characteristic device 26, and the actuators 28(1)-28(n) and communication network(s) 30 are described and illustrated herein, other types and/or numbers of systems, devices, components, and/or elements in other topologies can be used. It is to be understood that the systems of the examples described herein are for exemplary purposes, as many variations of the specific hardware and software used to implement the examples are possible, as will be appreciated by those skilled in the relevant art(s).

One or more of the treatment plan management computing apparatus 12, the plurality of client devices 14(1)-14(n), the plurality of practitioner devices 16(1)-16(n), and the plurality of caregiver devices 18(1)-18(n), for example, may be configured to operate as virtual instances on the same physical machine. In other words, one or more of the treatment plan management computing apparatus 12, practitioner devices 16(1)-16(n), caregiver devices 18(1)-18(n), or client devices 14(1)-14(n), may operate on the same physical device rather than as separate devices communicating through communication network(s) 30. Additionally, there may be more or fewer treatment plan management computing apparatus 12, practitioner devices 16(1)-16(n), caregiver devices 18(1)-18(n), or client devices 14(1)-14(n) than illustrated in FIG. 1.

In addition, two or more computing systems or devices can be substituted for any one of the systems or devices in any example. Accordingly, principles and advantages of distributed processing, such as redundancy and replication also can be implemented, as desired, to increase the robustness and performance of the devices and systems of the examples. The examples may also be implemented on computer system(s) that extend across any suitable network using any suitable interface mechanisms and traffic technologies, including by way of example only teletraffic in any suitable form (e.g., voice and modem), wireless traffic networks, cellular traffic networks, Packet Data Networks (PDNs), the Internet, intranets, and combinations thereof.

The examples may also be embodied as one or more non-transitory computer readable media having instructions stored thereon for one or more aspects of the present technology as described and illustrated by way of the examples herein. The instructions in some examples include executable code that, when executed by one or more processors, cause the processors to carry out steps necessary to implement the methods of the examples of this technology that are described and illustrated herein.

Referring to FIG. 3, a Unified Modeling Language (UML) use case diagram associated with an example of the companion application 68 that in this example is provided by the treatment plan management computing apparatus 28 is illustrated, although the companion application 68 may be obtained from other sources in other manners. In this example, solid line arrows indicate interactions with the users of the companion application 68 while the dotted line arrows indicate interactions through the system with actors that are not users of companion application 68. The gray bubbles in FIG. 3 refer to functions that have been disclosed in U.S. Provisional Patent Application No. 62/461,184 filed on Feb. 20, 2017 entitled "system and method for managing treatment plans," which is hereby incorporated in its entirety. The clear bubbles are capabilities that will be disclosed below. In FIG. 3, examples of functions that are provided by the companion application 68 include treatment based functions 200 and support/daily living skills functions 202, although other types and/or numbers of functions and/or other operations may be in each.

In one example, a caregiver associated with one of the caregiver devices 18(1)-18(n) and/or the client 208 associated with one of the client devices 14(1)-14(n) may use different instances of the companion application 68 on different devices. In another example, a caregiver associated with one of the caregiver devices 18(1)-18(n) and/or the client 208 associated with one of the client devices 14(1)-14(n) may share the same companion application 68 on the same device where capabilities may be limited via their login profile.

The companion application 68 may be used by the client 208 associated with one of the client devices 14(1)-14(n) for an extended period of time, supporting the client 208 associated with one of the client devices 14(1)-14(n) from early childhood into adulthood. As such the companion application 68 is designed to evolve with the client, which includes the flexibility to remotely upgrade the companion application 68 to include functionalities, games and features to evolve along with the capabilities of the client.

In one example, the practitioner(s) of the care team associated with one of the practitioner devices 16(1)-16(n) may prescribe adding/removing or modifying functions of the companion application 68 based on an analysis of the client which may be associated with one of the client devices 14(1)-14(n) by the treatment plan management device 12 as illustrated and described by way of the examples herein. Depending on the client, a related caregiver associated with one of the caregiver devices 18(1)-18(n) may be involved with using the companion application 68 for varying time periods. In one example, the client may be or eventually may become the only user of the companion application 68 relating to an ongoing behavioral treatment plan obtained from and managed by the treatment plan management computing apparatus 12. In another example, the caregiver(s) associated with one or more of the caregiver devices 18(1)-18(n) may be the user of the companion application 68 on behalf of the client, and in yet another example the caregiver associated with one of the caregiver devices 18(1)-18(n) and the client associated with one of the client devices 14(1)-14(n) may be co-users the companion application 68. In these illustrative examples, the treatment plan management computing apparatus 12 manages and coordinates all of these interactions with the different uses of the companion application 68 to accurately and adaptively monitor and advance the behavioral treatment plan for each related client.

In this particular example, most of the treatment related functions 200 that the behavioral interventionist associated with one of the practitioner devices 16(1)-16(n) and the caregiver associated with one of the caregiver devices 18(1)-18(n) have access to may be very similar in nature with the key difference being that the behavioral interventionist associated with one of the practitioner devices 16(1)-16(n) has the visibility to multiple clients, while the caregiver associated with one of the caregiver devices 18(1)-18(n) and/or client associated with one of the client devices 14(1)-14(n) only has access to a behavioral treatment plan data associated with that particular client via the companion application 68 managed by the treatment plan management computing apparatus 12.

In one example, the treatment-related functions 200 of the companion application 68 may include the following functions:

Select Client 212—may comprise programmed instructions that enable a behavioral interventionist associated with one of the practitioner devices 16(1)-16(n) to interact with the treatment plan management computing apparatus 12 to select and interact with respect to a behavioral treatment plan for a selected client.

Review Treatment Plan 212—may comprise programmed instructions that enable a client associated with one of the client devices 14(1)-14(n), a behavioral interventionist associated with one of the practitioner devices 16(1)-16(n), and/or a caregiver associated with one of the caregiver devices 18(1)-18(n) to obtain and review a current generated behavioral treatment plan assigned to the client and generated and managed by the treatment plan management computing apparatus 12.

Execute Treatment 214—may comprise programmed instructions that enable a client associated with one of the client devices 14(1)-14(n), a behavioral interventionist associated with one of the practitioner devices 16(1)-16(n), and/or a caregiver associated with one of the caregiver devices 18(1)-18(n) to execute instructions, such as one of a plurality of therapeutic techniques, e.g. one of a plurality of games or learning modules, related to a current generated behavioral treatment plan obtained from the treatment plan management computing apparatus 12.

Review Treatment Results 216—may comprise programmed instructions that enable a client associated with one of the client devices 14(1)-14(n), a behavioral interventionist associated with one of the practitioner devices 16(1)-16(n), and/or a caregiver associated with one of the caregiver devices 18(1)-18(n) to obtain and review current and past treatment results for the client from the treatment plan management computing apparatus 12.

Review Treatment History 218—may comprise programmed instructions that enable a client associated with one of the client devices 14(1)-14(n), a behavioral interventionist associated with one of the practitioner devices 16(1)-16(n), and/or a caregiver associated with one of the caregiver devices 18(1)-18(n) to study progress, issues, and/or trends of the client from the treatment plan management computing apparatus 12.

Messaging 220—may comprise programmed instructions that enable a client associated with one of the client devices 14(1)-14(n), a behavioral interventionist associated with one of the practitioner devices 16(1)-16(n), and/or a caregiver associated with one of the caregiver devices 18(1)-18(n) to communicate with other ones of the client at one of the client devices 14(1)-14(n), a behavioral interventionist associated with one of the practitioner devices 16(1)-16(n), a caregiver associated with one of the caregiver devices 18(1)-18(n), and/or the treatment plan management computing apparatus 12.

In-home Program 222—may comprise programmed instructions that enable a behavioral interventionist associated with one of the practitioner devices 16(1)-16(n) to assign in the generated behavioral treatment plan managed by the treatment plan management computing apparatus 12 one or more exercises ("In-home-Program") to be administered by the client. In one example, an In-home Program 222 may include practicing a new skill and/or a mastered skill in the generated behavioral treatment plan. By way of further example, instructions from the in-home program may be executed and displayed by one of the client devices 14(1)-14(n) or one of the caregiver devices 18(1)-18(n) and may show for example instructions to "Touch your left shoulder" and after the client associated with one of the client devices 14(1)-14(n) executes the treatment 214, the client at one of the client devices 14(1)-14(n) or a caregiver associated with one of the caregiver devices 18(1)-18(n) may report the results using the Report Treatment Results 216 functionality described earlier via a simple selection menu, such as designating observational data with respect to each treatment as "Independent", "With Help", "No Response", "Incorrect". This observational data is sent to the treatment plan management computing apparatus 12 for analysis to utilize for possible adjustments to the behavioral treatment plan.

Education Content 224—may comprise programmed instructions that enable a client associated with one of the client devices 14(1)-14(n) and/or a caregiver associated with one of the caregiver devices 18(1)-18(n) to download and access educational content related to the behavioral treatment plan from the treatment plan management computing apparatus 12, such as educational html pages, PDFs, videos, and/or audio by way of example only.

Manage Appointments 224—may comprise programmed instructions that enable a client associated with one of the client devices 14(1)-14(n) and/or a caregiver associated with one of the caregiver devices 18(1)-18(n) to interact with the treatment pan management computing apparatus 12 to manage treatment appointments 226 with the behavioral interventionist associated with one of the practitioner devices 16(1)-16(n), such as scheduling, reviewing, and modifying of appointments by way of example only.

Others—may comprise programmed instructions that enable a client associated with one of the client devices 14(1)-14(n), a behavioral interventionist associated with one of the practitioner devices 16(1)-16(n), and/or a caregiver associated with one of the caregiver devices 18(1)-18(n) to interact with the treatment plan management computing apparatus 12 and to adjust and/or add to any of these functions based on the managed assessment of the client over time.

Support/Daily Living Skills 202:

Scheduling 230—may comprise programmed instructions that enable a client associated with one of the client devices 14(1)-14(n), a behavioral interventionist associated with one of the practitioner devices 16(1)-16(n), and/or a caregiver associated with one of the caregiver devices 18(1)-18(n) to set up calendar events related to the behavioral treatment plan managed by the treatment plan management computing apparatus.

Reminders/Coaching 234—may comprise programmed instructions that enable a client associated with one of the client devices 14(1)-14(n) and/or a caregiver associated with one of the caregiver devices 18(1)-18(n) to set up reminders of therapeutic techniques, such as scheduled events to prompt the client regarding one or more daily living activities that may normally be a challenge to the client. In another example, these may comprise programmed instructions that enable a client associated with one of the client devices 14(1)-14(n) and/or a caregiver associated with one of the caregiver devices 18(1)-18(n) to obtaining coaching content from the treatment plan management computing apparatus 12 to reinforce certain required skills on for example a pre-scheduled or a recurring basis.

Major Event Recording 234—may comprise programmed instructions that enable a client associated with one of the client devices 14(1)-14(n) and/or a caregiver associated with one of the caregiver devices 18(1)-18(n) to record observational data regarding significant events, e.g., doctor visits, health issues, or meltdown events by way of example only, to a behavioral interventionist associated with one of the practitioner devices 16(1)-16(n) and/or the treatment plan management computing apparatus 12. Observation data about the events may be stored for the client in a medical record by the treatment plan management computing apparatus 12 in the memory 42 and may be made available for consideration by for example the behavioral interventionist associated with one of the practitioner devices 16(1)-16(n) and/or by the artificial intelligence module 54 to analyze for possible adjustments to the behavioral treatment plan.

Sensor data collection 236—may comprise programmed instructions that enable one of the client devices 14(1)-14(n), one of the practitioner devices 16(1)-16(n), one of the caregiver devices 18(1)-18(n), and/or the treatment plan management computing apparatus 12 to integrate with and obtain data from one or more of the sensors, such as biomarker sensor 20, movement sensor 21, video recorder 22, microphone 23, and/or environmental sensor 24 by way of example only. Sensor data may be collected for or by the treatment plan management computing apparatus 12 for analysis and inclusion adjusting behavioral treatment plans. In one example, sensors may monitor a current surrounding environment of the client within a defined proximity.

Support Network 228—may comprise programmed instructions that enable the enable one of the client devices 14(1)-14(n) and/or one of the caregiver devices 18(1)-18(n) to interact with an on-line support network where useful information and experiences, with peers and subject matter experts may be shared and obtained.

Virtual Assistant 240—may comprise programmed instructions that enable one of the client devices 14(1)-14(n) and/or one of the caregiver devices 18(1)-18(n) interaction with a virtual assistant provided in conjunction with the treatment management computing apparatus 12 to assist with questions, such as questions regarding a treatment related functions or regarding support/daily living support functions for the client.

Interactive Games 242—may comprise programmed instructions that enable one of the client devices 14(1)-14(n) and/or one of the caregiver devices 18(1)-18(n) to provide games and other interactive online activities as part of the generated behavioral treatment plan. Execution of one or more games or other interactive online activities at different times may comprise additional therapeutic techniques of the generated behavioral treatment plan that may calm down the client and manage levels of anxiety.

Distress Tolerance Apps 244—may comprise programmed instructions that enable distress tolerance content to be executed and provided to a client associated with one of the client devices 14(1)-14(n) and/or a caregiver associated with one of the caregiver devices 18(1)-18(n) to help calm a client down when anxiety builds up. In one example, this may be implemented by functions that guide the client associated with one of the client devices 14(1)-14(n) through a known set of exercises (for example, breathing exercises based on instructions). In another example, these functions may include a mindfulness exercises. In yet another example these functions may for example play calming music or displaying familiar photos via one of the client devices 14(1)-14(n) and/or one of the caregiver devices 18(1)-18(n).

Emergency Hotline 246—may comprise programmed instructions that enable the client associated with one of the client devices 14(1)-14(n) and/or one of the caregiver devices 18(1)-18(n) to contact a crisis team that may assist them in difficult times, e.g., when the client has a meltdown. In response, one of the practitioners associated with one of the practitioner devices 16(1)-16(n) and/or one of the caregivers associated with one of the caregiver devices 18(1)-18(n) may be electronically notified of the intervention and may provide executable instructions for assisting with an intervention, such as providing coaching instructions for assisting the client through the situation.

Billing Management 248—may comprise programmed instructions that enable allows the client associated with one of the client devices 14(1)-14(n) and/or the caregiver associated with one of the caregiver devices 18(1)-18(n) to manage their medical bills associated with the treatment, such as viewing a payment history or making a co-payment by way of example.

Career Support 250—may comprise programmed instructions that enable the client associated with one of the client devices 14(1)-14(n) and/or the caregiver associated with one of the caregiver devices 18(1)-18(n) to access to career resources managed by the treatment plan management computing apparatus that are specifically tailored for a person with particular condition, such as ASD by way of example.

Location 252—may comprise programmed instructions that enable one of the client devices 14(1)-14(n) and/or one of the caregiver devices 18(1)-18(n) to have the ability to identify the location of a client, e.g., via a Global Positioning System (GPS), and to report this location to one or more of the practitioner associated with one of the practitioner devices 16(1)-16(n), the caregiver associated with one of the caregiver devices 18(1)-18(n) and/or the treatment plan management computing apparatus 12, such as by a text message, phone call or email by way of example only, managed by the treatment plan management computing apparatus 12. In one example rules may be configured and managed by the treatment plan management computing apparatus 12 to define an expected location of a client at given times and alerts may be configured to be generated and sent to the practitioner associated with one of the practitioner devices 16(1)-16(n) and/or the caregiver associated with one of the caregiver devices 18(1)-18(n) and/or when a client moves outside a specific predefined range of a particular environment setting.

Others—may comprise programmed instructions that enable a client associated with one of the client devices 14(1)-14(n), a behavioral interventionist associated with one of the practitioner devices 16(1)-16(n), and/or a caregiver associated with one of the caregiver devices 18(1)-18(n) to interact with the treatment plan management computing apparatus 12 and to adjust and/or add to any of these functions based on the managed assessment of the client over time.

Exemplary methods for managing behavioral treatment therapy will now be described with reference to FIGS. 1-7. In the examples illustrated and described herein, a client is a person with ASD or any other condition or other disorder which may benefit from ongoing behavioral therapy programs directed to reducing associated deficits and behaviors, thereby increasing the quality of life and functional independence of affected individuals.

Figure 4:
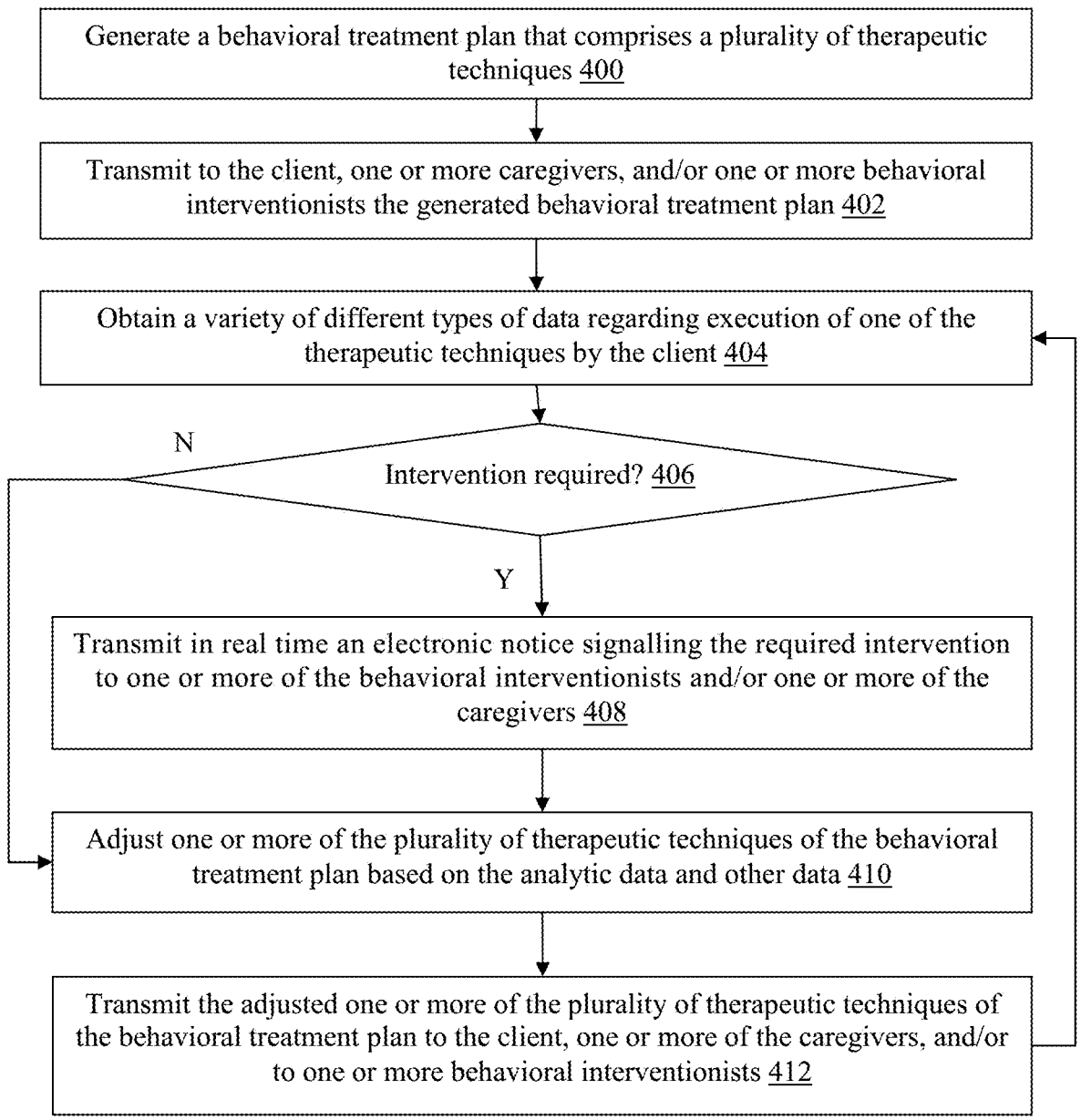
FIG. 4 is a flowchart of an example of a method for managing behavioral treatment therapy that is intended to be used by clients, caregivers, and practitioners to more effectively support continuous and ongoing home and community care in the healthcare industry.

Referring more specifically to FIG. 4, in this example in step 400, the treatment plan management computing device 12 may generate a behavioral treatment plan that comprises a plurality of therapeutic techniques to be carried out in a specified manner and/or progressive order for one of a plurality clients that each may be associated with one of the plurality of client devices 14(1)-14(n). The treatment plan management computing device 12 may analyze evaluation data and/or other obtained data, such as biomarker data, environmental characteristic data, recorded movement data, video data, and/or audio data by way of example only, related to the client as well as stored treatment plans in treatment plan database 50, by way of example only, to generate a behavioral treatment plan comprising a plurality of therapeutic techniques for the client. In this example, the biomarker data may comprise one or more of heart rate, respiration, body temperature or anxiety level and the environmental data may comprise one or more of a temperature reading, a pressure reading, or lighting level reading. In particular, the treatment plan management computing device 12 has uniquely identified, monitored and utilized a variety of different types of data that have not previously been considered in the combinations described by way of the examples herein.

Additionally, the treatment plan management computing device 12 may optionally execute artificial intelligence module 54 to apply machine learning on, for example, the evaluation data and/or other obtained data and treatment plan data discussed above for the client discussed above as well as on other stored evaluation data and/or other obtained data as well as other treatment plans for other clients in the treatment database 50 and the client records database 52, by way of example only. The artificial intelligence module 54 may be configured in a number of different manners to identify cross-correlations between clients, obtained and stored data, treatment plans and/or therapeutic techniques and then use these to learn and make ongoing adjustments which is not well understood, routine or conventional in this technology space to provide this level of cross-correlated insight for adjusting treatment plans and/or therapeutic techniques. Additionally, the artificial intelligence module 54 may be configured to enables the cross-correlation of treatment plans for clients along multiple levels, such as clients with different conditions, but other similarities with for example aspects of the treatment plan and/or the condition being treated or with other relating characteristics, such as age, health, and/or social determinant data, to enable more effective integration of past feedback data when customizing behavioral treatment plans.

In step 402, the treatment plan management computing device 12 may transmit to the client associated with one of the client devices 14(1)-14(n), to one or more behavioral interventionist associated with one or more of the practitioner devices 16(1)-16(n), and/or to one or more of the related caregivers associated with one of the caregiver devices 18(1)-18(n) the generated behavioral treatment plan comprising a plurality of therapeutic techniques.

In step 404, the treatment plan management computing device 12 may obtain analytic data regarding execution of one of the therapeutic techniques by the client from the one of the client devices 14(1)-14(n), one or more of the caregivers associated with one of the caregiver devices 18(1)-18(n), and/or to one or more behavioral interventionist associated with one or more of the practitioner devices 16(1)-16(n). In particular, the analytic data may comprise observational and/or other recorded evaluation data of cognitive and/or behavioral types of responses from the client during execution of one or more of the therapeutic techniques provided by one of the client devices 14(1)-14(n), one or more of the practitioner devices 16(1)-16(n), and/or one of the caregiver devices 18(1)-18(n), although other types of analytic data may be obtained. In addition to the analytic data related to observational and/or other recorded evaluation data of the cognitive and/or behavioral types of responses from the client during execution of one or more of the therapeutic techniques, the treatment plan management computing apparatus 12 is able to utilize a variety of other types and/or numbers of other types of data and in different combinations that may be utilized to generate and/or adjust the treatment plan and/or therapeutic techniques.

By way of example only, the treatment plan management computing apparatus 12 also may obtain biomarker data from monitoring biomarkers of the client during the execution of one or more of the therapeutic techniques. The biomarker data may comprise data on heart rate, respiration, body temperature, or anxiety level of the client during the execution of one or more of the therapeutic techniques by the client, although other numbers and/or types of biomarker data may be obtained and utilized. The biomarker data may be obtained by one or more biomarker sensor(s) 20 coupled to the client, such as by a wearable biomarker sensor, although the biomarker data may be obtained in other manners. The biomarker data may be collected directly from the biomarker sensor 20 by the treatment plan management computing apparatus 12 or from other sources, such as by one of the client devices 14(1)-14(n), one or more of the practitioner devices 16(1)-16(n), and/or one of the caregiver devices 18(1)-18(n) by way of example only.

By way of example only, the treatment plan management computing apparatus 12 may analyze different combinations of the biomarker data to obtain additional biomarker data, such as obtaining an anxiety level based on a combination of measure heart rate and perspiration of the client based on stored tables correlating those reading to anxiety levels. By way of further example, the treatment plan management computing apparatus 12 may apply a weighting factor to one or more biomarker data reading when correlating to an anxiety level, such as taking into account a reading of an environmental characteristic of current temperature and then reducing the weight of a perspiration reading if the temperature reading is above a threshold temperature, e.g. ninety degrees Fahrenheit.

The treatment plan management computing apparatus 12 also may obtain environmental characteristic data during the execution of one or more of the therapeutic techniques. By way of example only, the environmental characteristic data may comprise a temperature reading, a pressure reading, or lighting level reading, although other types and/or numbers of environmental characteristic data may be obtained. By way of example only, environmental characteristic data may also be obtained by the treatment plan management computing apparatus 12 from input environmental data by for example one of the caregivers at one of the caregiver devices 18(1)-18(n) or from connecting to an third party server and requesting and receiving environmental characteristic data, although other types and/or amounts of environmental characteristic data may be obtained and from other sources. In this example, the environmental characteristic data is obtained by monitoring with environmental sensor(s) 24 in residential community building 32 where the one of the therapeutic techniques is executed by the client and is provided to the treatment plan management computing apparatus 12.

The treatment plan management computing apparatus 12 may obtain audio and/or video data, such as audio or video from at least one of a microphone or video recorder, from monitoring during the execution of at least one of the therapeutic techniques by the client. In this example, the audio and/or video data provides the treatment plan management computing apparatus 12 beyond the analytic data comprising the cognitive and/or behavioral types of responses from the client during execution of one or more of the therapeutic techniques. By way of example only, the audio and video data may each provide the treatment plan management computing apparatus 12 with a variety of individual and overall data points, such as audio data on one or more sound bursts above a set threshold and their duration, audio data on average overall sound levels, overall video data on what was in the environment, and specific video data on particular changes in the environment by way of example only, which can be correlated by the treatment plan management computing apparatus 12 with other data to make determinations on any changes or updates to the behavioral treatment plan and/or any of the therapeutic techniques. By way of example, with the combination of the analytic data comprising the cognitive and/or behavioral types of responses from the client during execution of one or more of the therapeutic techniques and the audio and/or video data, the treatment plan management computing apparatus 12 may be able to identify particular sounds, sound pattern, or other events that positively and/or negatively influenced execution of part or all of a therapeutic technique and may adjust the treatment plan and/or one or more therapeutic techniques, such as introducing white noise with certain future therapeutic techniques.

The treatment plan management computing apparatus 12 may obtain movement data of the client from monitoring during the execution of one of the therapeutic techniques by the client. By way of example only, the movement data may comprise overall movement of the client during the execution of at least one of the therapeutic techniques or may comprise movement data related to a particular body part or parts of the client during the execution of at least one of the therapeutic techniques. The treatment plan management computing apparatus 12 may utilize the movement data to detect stimming, by way of example only, and then may combine or otherwise correlate with the analytic data comprising the cognitive and/or behavioral types of responses from the client during execution of one or more of the therapeutic techniques to again adjust the treatment plan and/or therapeutic techniques.

The treatment plan management computing apparatus 12 may also identify social determinants data about the client from the client at one of the client devices 14(1)-14(n) or one of the caregivers at one of the caregiver devices 18(1)-18(n), although the social determinants data can be obtained in other manners. Again the treatment plan management computing apparatus 12 may utilize the social determinants data in combination or otherwise correlated with the analytic data comprising the cognitive and/or behavioral types of responses from the client during execution of one or more of the therapeutic techniques to again adjust the treatment plan and/or therapeutic technique In step 406, the treatment plan management computing device 12 may determine when an intervention in the behavioral treatment plan is required based on the obtained data in step 404. By way of example only, one or more elements of data may be compared against stored and/or customized thresholds for the client to identify an anomaly that may indicate a meltdown of the client may occur. If in step 406, the treatment plan management computing device 12 determines an intervention in the behavioral treatment plan is not required then the No branch is taken back to step 404 as described earlier.

If in step 406, the treatment plan management computing device 12 determines an intervention in the behavioral treatment plan is required then the Yes branch is taken back to step 408. In step 408, the treatment plan management computing device 12 transmits in real time an electronic notice signalling the intervention along with one or more instructions and/or alternative therapeutic techniques to try and implement with the client, such as playing music, displaying pictures of friends, or redirecting to an online game by way of example only, to one or more of the behavioral interventionists associated with one or more of the practitioner devices 16(1)-16(n) or one or more of the caregivers associated with one of the caregiver devices 18(1)-18(n). Coordination with designated actuators, such as one or more of actuators 28(1)-28(n) which are coupled to control aspects of a variety of different types of devices by the treatment plan management computing device 12 in managing treatment plans and/or therapeutic techniques is not well understood, routine or conventional in this technology space and provides substantially enhanced results with ongoing treatments.

In step 412, the treatment plan management computing device 12 may adjust the entire behavioral treatment plan or may adjust one or more of the plurality of therapeutic techniques of the behavioral treatment plan based on the one or more of the examples of obtained data in step 404 including analytic data, biomarker data, environmental characteristic data, audio and/or video data, movement data, and/or social determinants data in various combinations or other correlations with other information, such as stored behavioral treatment plan templates each with different therapeutic techniques and stored client records. In this example, the treatment plan management computing device 12 may execute the artificial intelligence module 54 to analyze with machine learning techniques obtained data for the client as well as other obtained data from other clients which are correlated to the current client, such as because they are being treated for the same type of condition, along with the treatment plan data in the treatment plan database to earn and extract appropriate recommended adjustments and/or update to the entire behavioral treatment plan and/or may to one or more of the plurality of therapeutic techniques. By way of example only, the treatment plan management computing device 12 may analyze obtained biomarker data individually and/or in combination to generated new biomarker data, such as an anxiety level reading based on for example a heart rate reading and a perspiration reading to determine adjustments. By way of further example only, the treatment plan management computing device 12 may adjust the calculation of the anxiety level reading based on obtained environmental characteristic data on a temperature reading, such as reducing a weighted significance of a perspiration reading as a temperature reading goes above a stored threshold temperature which is not well understood, routine or conventional in this technology space and provides unique insights for making adjustments to ongoing treatment plans and/or therapeutic techniques. Additionally, he treatment plan management computing device 12 may adjust based on different types of environmental characteristic readings, such as atmospheric pressure readings or light level readings which is not well understood, routine or conventional in this technology space. Further, the treatment plan management computing device 12 may adjust one or more of the plurality of therapeutic techniques of the behavioral treatment plan based on obtained movement data. In one example, the treatment plan management computing device 12 may identify any stimming from the movement data and adjust the one or more of the plurality of therapeutic techniques of the behavioral treatment plan based on any of the identified stimming from the movement data. The treatment plan management computing device 12 may adjust one or more of the plurality of therapeutic techniques of the behavioral treatment plan based on the obtained observational data and/or based on the social determinants data.

The treatment plan management computing device 12 also may adjust one or more of the plurality of therapeutic techniques of the behavioral treatment plan to add in one or more instructions that is/are configured to adjust one or more actuators each coupled to control a different device associated with the client. By way of example, the instruction may comprise a pressure adjustment instruction that is configured to adjust a pressure actuator coupled to control a pressure device associated with the client which is not well understood, routine or conventional in this technology space. By way of another example the instruction may comprise an environmental characteristic instruction that is configured to adjust an environmental actuator that is coupled to control an environmental characteristic device in a surrounding area associated with the client based on the obtained location data, such as increasing or decreasing temperature with a thermostat or increasing or decreasing a lighting level with a light device, which is not well understood, routine or conventional in this technology space to provide enhance adjustable controls of environments during execution of therapeutic techniques resulting in greater and faster by the client.

Further, the treatment plan management computing device 12 may adjust one or more of the plurality of therapeutic techniques of the behavioral treatment plan based on obtained audio or video of the client during the execution of at least one of the therapeutic techniques. By way of example only, the treatment plan management computing apparatus 12 may use the obtained audio and/or video data, such as audio data on one or more sound bursts above a set threshold and their duration, audio data on average overall sound levels, overall video data on what was in the environment, and specific video data on particular changes in the environment by way of example only, to identify and change a sequence, type, and/or location of execution of therapeutic techniques, such as having a client utilize headphones or ear plugs, change a location of the treatment, and/or to change the viewing perspective of the client at an existing location towards a less visually stimulating direction or towards a calming target.

In step 412, the treatment plan management computing device 12 may transmit the adjusted one or more of the plurality of therapeutic techniques of the behavioral treatment plan to the client one of the client devices 14(1)-14(n), one or more of the caregivers associated with one of the caregiver devices 18(1)-18(n), and/or to one or more behavioral interventionist associated with one or more of the practitioner devices 16(1)-16(n). Prior to transmitting, the treatment plan management computing device 12 may optionally determine which of the adjusted one or more of the plurality of therapeutic techniques of the behavioral treatment plan to be completed are to be carried out by to one or more behavioral interventionist associated with one or more of the practitioner devices 16(1)-16(n) or by the client one of the client devices 14(1)-14(n) or one or more of the caregivers associated with one of the caregiver devices 18(1)-18(n) which is not well understood, routine or conventional in this technology space and provides more directed instruction for assisting a client. Each of the adjusted one or more of the plurality of therapeutic techniques of the behavioral treatment plan may then be transmitted by the treatment plan management computing device 12 to either the one of the one or more of the practitioner devices 16(1)-16(n) or by the client one of the client devices 14(1)-14(n) or one or more of the caregivers associated with one of the caregiver devices 18(1)-18(n) based on the determination.

Figure 5:
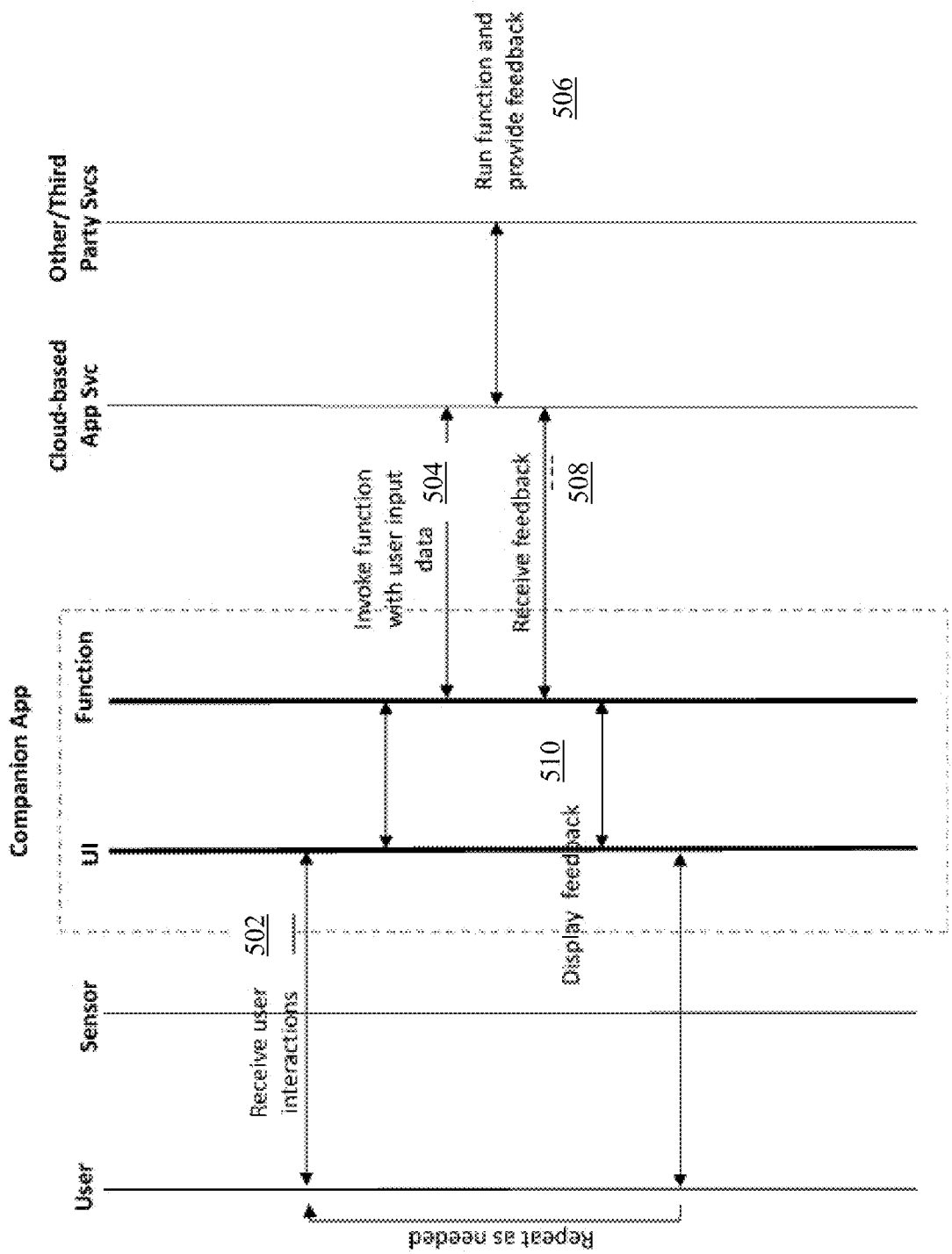
FIG. 5 is a sequence diagram of another example of a method for managing behavioral treatment therapy that incorporates analytic data from execution of a client therapeutic technique comprising a game with the companion application.

Referring to FIG. 5, a sequence diagram of another example of a method for managing behavioral treatment therapy that incorporates analytic data from execution of a client therapeutic technique comprising a game with the companion application 68 is illustrated. In this example, at step 502 the companion application 68 may receive an interaction invoking, for example, one of the functions illustrated and described by way of example only with reference to FIG. 3 from the client associated with one of the client devices 14(1)-14(n) and/or the caregiver associated with one of the caregiver devices 18(1)-18(n) via a User Interface (UI).

In step 504, upon receiving the interaction invoking, for example, one of the functions illustrated and described by way of example only with reference to FIG. 3, the one of the client devices 14(1)-14(n) or the one of the caregiver devices 18(1)-18(n) routes a corresponding requests via the Cloud-based App servers to application specific back-end services or the treatment plan management computing apparatus 12.

In step 506, application specific back-end services or the treatment plan management computing apparatus 12 sends the requested content or services associated with the invoked one of the functions to the one of the client devices 14(1)-14(n) or the one of the caregiver devices 18(1)-18(n) in this example.

In step 508, the requesting one of the client devices 14(1)-14(n) or the one of the caregiver devices 18(1)-18(n) receives the requested content or services. In step 510, the requesting one of the client devices 14(1)-14(n) or the one of the caregiver devices 18(1)-18(n) may then process the received content or service based on the initially invoked function. Steps 502-510 may be repeated by the one of the client devices 14(1)-14(n) or the one of the caregiver devices 18(1)-18(n) as needed.

Figure 6:
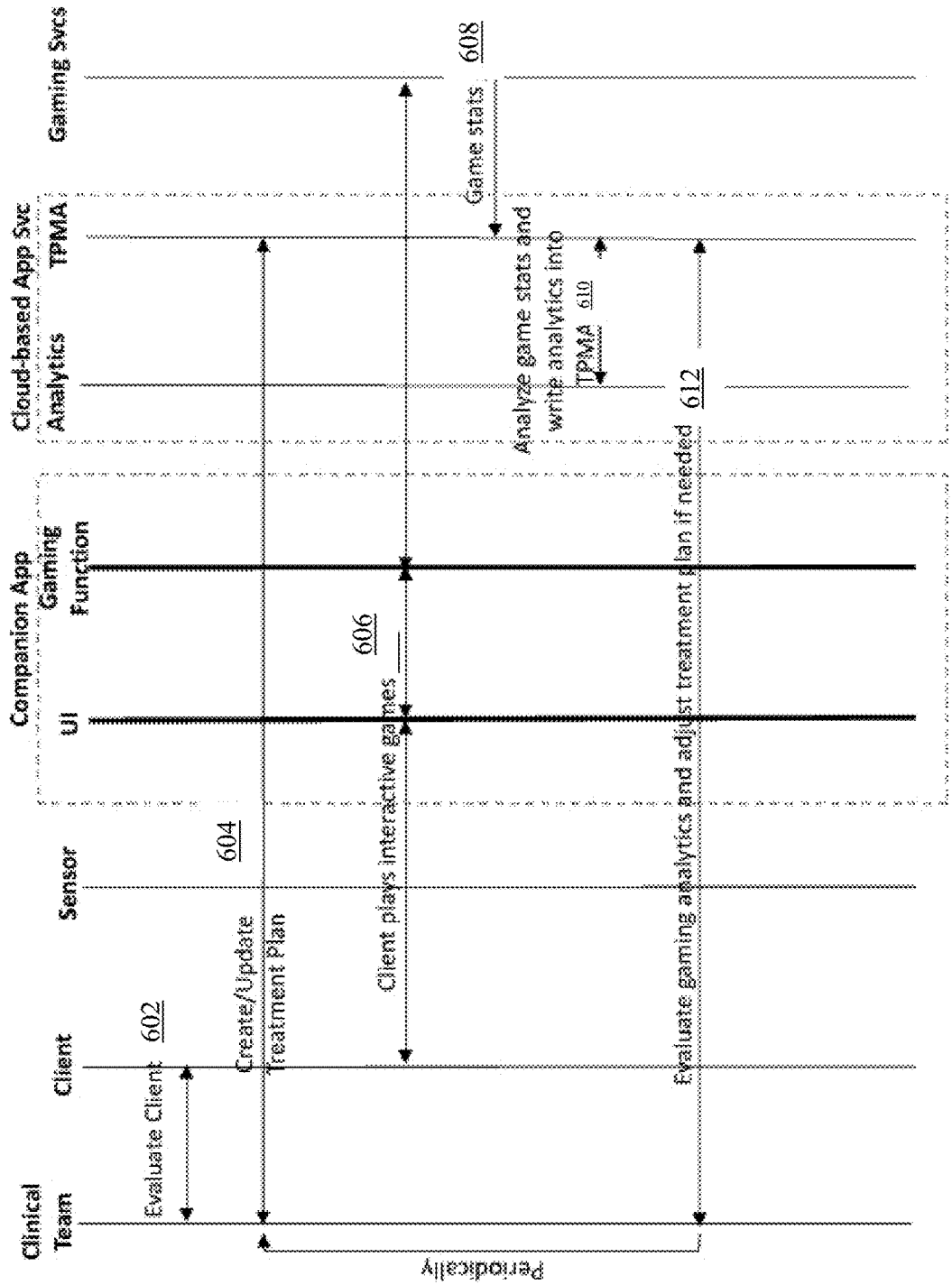
FIG. 6 is a sequence diagram of an example of a method for managing execution of the client therapeutic technique comprising the game with the companion application utilized in the example in FIG. 5.

Referring to FIG. 6, a sequence diagram of an example of a method for managing behavioral treatment therapy where a game is utilized as a therapeutic technique is illustrated. In step 602, data, such as observational data, medical history data, biomarker data, and/or surrounding environmental data by way of example only, relating to a condition for which a client may require behavioral therapy is obtained and forwarded by one of the client devices 14(1)-14(n), one of the practitioner devices 16(1)-16(n) or the one of the caregiver devices 18(1)-18(n) to the treatment plan management computing apparatus 12.

In step 604, the treatment plan management computing apparatus 12 evaluates the obtain data and either generates or otherwise identifies and obtains a behavioral treatment plan or adjusts a behavioral treatment plan based on the received obtained data. By way of example only, the behavioral treatment plan may comprise a plurality of therapeutic techniques, one of which may comprise a game or other interactive online activity for the client to execute as part of the behavioral treatment plan. This behavioral treatment plan may be provided by the treatment plan management computing apparatus 12 to the one of the client devices 14(1)-14(n), one of the practitioner devices 16(1)-16(n), or the one of the caregiver devices 18(1)-18(n) for execution of the game or other online activity.

In step 606, the client at one of the client devices 14(1)-14(n) or one of the caregiver devices 18(1)-18(n) plays the game or online activity and statistical data related to the interaction with that game or online activity is captured and provided to the treatment plan management computing apparatus 12.

In step 608, the treatment plan management computing apparatus 12 may record the statistical data related to the interaction with that game or online activity in the client records database 52, by way of example only, for future use for adjusting the behavioral treatment plan for that client and other related clients by the artificial intelligence module 54, by way of example only.

In step 610, the treatment plan management computing apparatus 12 may analyze the stored statistical data for the client and may analyze other stored statistical data for other related clients utilizing the artificial intelligence module 54, by way of example only, to determine if an adjustment of the behavioral treatment plan for that client is required.

In step 612, the treatment plan management computing apparatus 12 may adjust the behavioral treatment plan for the client based on the analysis in step 610.

Figure 7:
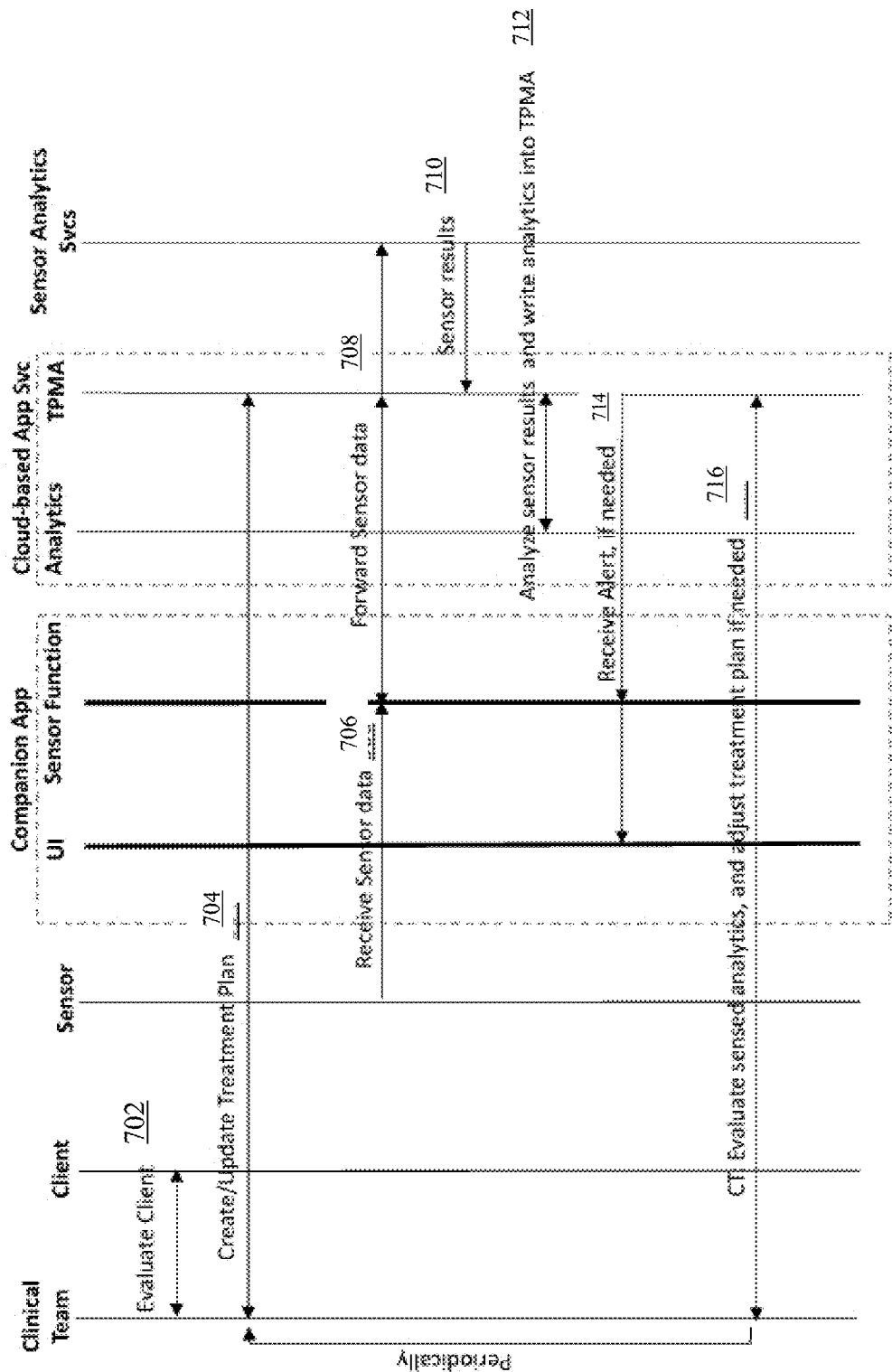
FIG. 7 is a sequence diagram of yet another example of a method for managing behavioral treatment therapy that incorporates sensor data.

Referring to FIG. 7, a sequence diagram of yet another example of a method for managing behavioral treatment therapy that incorporates sensor data is illustrated. In step 702, data, such as observational data, medical history data, biomarker data, and/or surrounding environmental data by way of example only, relating to a condition for which a client may require behavioral therapy is obtained and forwarded by one of the client devices 14(1)-14(n), one of the practitioner devices 16(1)-16(n) or the one of the caregiver devices 18(1)-18(n) to the treatment plan management computing apparatus 12.

In step 704, the treatment plan management computing apparatus 12 evaluates the obtain data and either generates or otherwise identifies and obtains a behavioral treatment plan or adjusts a behavioral treatment plan based on the received obtained data. This behavioral treatment plan may be provided by the treatment plan management computing apparatus 12 to the one of the client devices 14(1)-14(n), one of the practitioner devices 16(1)-16(n), or the one of the caregiver devices 18(1)-18(n) for execution of the next one of the plurality of therapeutic techniques in the plan.

In step 706, one of the client devices 14(1)-14(n), one of the practitioner devices 16(1)-16(n), or one of the caregiver devices 18(1)-18(n) may collect from one or more of the sensors, such as biomarker sensor 20, movement sensor 21, video recorder 22, microphone 23, and/or environmental sensor 24 by way of example only, sensor data related to the client during execution of one of the plurality of therapeutic techniques. By way of example only, sensor data may comprise biomarker data, environmental characteristic data and other movement and/or videos or audio data.

In step 708, one of the client devices 14(1)-14(n), one of the practitioner devices 16(1)-16(n), or one of the caregiver devices 18(1)-18(n) may forward the collected sensor data to the treatment plan management computing apparatus 12, although the sensor data may be obtained in other manners. For example the treatment plan management computing apparatus 12 may receive the collected sensor data directly from one or more of the sensors.

In step 710, the treatment plan management computing apparatus 12 may receive the collected sensor data from one of the client devices 14(1)-14(n), one of the practitioner devices 16(1)-16(n), or one of the caregiver devices 18(1)-18(n).

In step 712, the treatment plan management computing apparatus 12 may analyze the received sensor data, such as with the artificial intelligence module 54, by way of example only, to determine if any adjustments to the behavioral treatment plan are required, although others approaches for analyzing the sensor data may be used.

In step 714, the treatment plan management computing apparatus 12 also may receive an alert regarding the collected data and may need to analyze and determine if an electronic notification regarding an intervention needs to be generated and transmitted to one or more of one of the practitioner devices 16(1)-16(n) or one of the caregiver devices 18(1)-18(n).

In step 716, the treatment plan management computing apparatus 12 may transmit the adjusted behavioral treatment plan based on the obtained senor data to one of the client devices 14(1)-14(n), one of the practitioner devices 16(1)-16(n), or one of the caregiver devices 18(1)-18(n).

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefore, is not intended to limit the claimed processes to any order except as may be specified in the claims. Accordingly, the invention is limited only by the following claims and equivalents thereto.

What is claimed is:

1. A method for managing behavioral treatment therapy, the method implemented by a computing device, the method comprising:

generating a treatment plan comprising a plurality of therapeutic techniques that is transmitted to at least one of a client at a client device or a practitioner at a practitioner device associated with the client;

obtaining analytic data regarding execution of at least one of the therapeutic techniques from at least one of the client device or the practitioner device, biomarker data from at least one biomarker sensor coupled to the client, environmental data from at least one environmental characteristic sensor, and environmental audiovisual data at a location of and external from the client during execution of the at least one of the therapeutic techniques;

adjusting one or more of the plurality of therapeutic techniques of the treatment plan based on the analytic data, the biomarker data, and the environmental data, wherein the adjusting the one or more of the plurality of therapeutic techniques of the treatment plan is further based on any threshold based changes in the environmental audiovisual data from any prior location of execution of the one or more therapeutic techniques for the client, wherein the adjusting further comprises:

employing artificial intelligence to analyze the obtained analytic data, biomarker data, and environmental data for the client, additional obtained analytic data, biomarker data, and environmental data of one or more other clients correlated to the client based on a corresponding one of a plurality of types of conditions, and further additional obtained analytic data, biomarker data, and environmental data of one or more other additional clients having an uncorrelated one of the plurality of types of conditions to the client with two or more other correlated aspects to adjust the one or more of the plurality of therapeutic techniques of the treatment plan, wherein the two or more other correlated aspects comprise treatment plans, age, or social determinant data; and transmitting the adjusted one or more of the plurality of therapeutic techniques of the treatment plan to at least one of the client device or the practitioner device.

2. The method as set forth in claim 1 wherein the obtaining further comprises:

obtaining at least movement data from at least one movement sensor monitoring the client during the execution of at least one of the therapeutic techniques;

wherein the adjusting the one or more of the plurality of therapeutic techniques of the treatment plan is further based on the obtained movement data.

3. The method as set forth in claim 2 further comprises:
identifying any stimming from the movement data;
wherein the adjusting the one or more of the plurality of therapeutic techniques of the treatment plan is further based on any of the identified stimming from the movement data.

4. The method as set forth in claim 1 wherein the obtaining further comprises:

obtaining from at least one caregiver device observational data from monitoring the client during the execution of at least one of the therapeutic techniques;

wherein the adjusting the one or more of the plurality of therapeutic techniques of the treatment plan is further based on the obtained observational data.

5. The method as set forth in claim 1 wherein the biomarker data comprises one or more of heart rate, respiration, body temperature or anxiety level and wherein the environmental data comprises one or more of a temperature reading, a pressure reading, or lighting level reading.

6. The method as set forth in claim 1 wherein the adjusting the one or more of the plurality of therapeutic techniques further comprises;

adding an instruction that is configured to adjust at least one actuator coupled to control a device associated with the client.

7. The method as set forth in claim 6 wherein the instruction further comprises a pressure adjustment instruction that is configured to adjust a pressure actuator coupled to control a pressure device associated with the client.

8. The method as set forth in claim 6 wherein the obtaining further comprises:

Obtaining a current location of the client from at least one of the client device or the practitioner device;

wherein the instruction further comprises an environmental characteristic instruction that is configured to adjust an environmental actuator that is coupled to control an environmental characteristic device in a surrounding area associated with the client based on the obtained current location.

9. The method as set forth in claim 1 further comprising:
determining when an intervention in the treatment plan is required based on the analytic data and at least one of the biomarker data or the environmental data; and transmitting in real time an electronic notice signaling the intervention to at least one of the practitioner device, a caregiver device, or the client device when the determination indicates the intervention is required.

10. The method as set forth in claim 1 wherein the transmitting the adjusted one or more of the plurality of therapeutic techniques of the treatment plan further comprises:

determining which of the adjusted one or more of the plurality of therapeutic techniques of the treatment plan are to be carried out by the practitioner device or one of the at least one of the client device or a caregiver device; and transmitting each of the adjusted one or more of the plurality of therapeutic techniques of the treatment plan to either the practitioner device or one of the at least one of the client device or the caregiver device based on the determination.

11. An apparatus comprising:
a processor; and
a memory coupled to the processor which is configured to be capable of executing programmed instructions comprising and stored in the memory to:

generate a treatment plan comprising a plurality of therapeutic techniques that is transmitted to at least one of a client at a client device or a practitioner at a practitioner device associated with the client;

obtain analytic data regarding execution of at least one of the therapeutic techniques from at least one of the client device or the practitioner device, biomarker data from at least one biomarker sensor coupled to the client, environmental data from at least one environmental characteristic sensor, and environmental audiovisual data at a location of and external from the client during execution of the at least one of the therapeutic techniques;

adjust one or more of the plurality of therapeutic techniques of the treatment plan based on the obtained analytic data, the biomarker data, the environmental data, and the environmental audiovisual data at the location of and external from the client, wherein the adjust the one or more of the plurality of therapeutic techniques of the treatment plan is further based on any threshold based changes in the environmental audiovisual data from any prior location of execution of the one or more therapeutic techniques for the client, wherein the adjust further comprises:

employing artificial intelligence to analyze the obtained analytic data, biomarker data, and environmental data for the client, additional obtained analytic data, biomarker data, and environmental data of one or more other clients correlated to the client based on a corresponding one of a plurality of types of conditions, and further additional obtained analytic data, biomarker data, and environmental data of one or more other additional clients having an uncorrelated one of the plurality of types of conditions to the client with two or more other correlated aspects to adjust the one or more of the plurality of therapeutic techniques of the treatment plan, wherein the two or more other correlated aspects comprise treatment plans, age, or social determinant data; and transmit the adjusted one or more of the plurality of therapeutic techniques of the treatment plan to at least one of the client device or the practitioner device.

12. The apparatus as set forth in claim 11 wherein for the obtain analytic data and at least one of biomarker data from at least one biomarker sensor or environmental data the processor is further configured to be capable of executing the stored programmed instructions to:

obtain at least movement data from at least one movement sensor monitoring the client during the execution of at least one of the therapeutic techniques;

wherein the adjust the one or more of the plurality of therapeutic techniques of the treatment plan is further based on the obtained movement data.

13. The apparatus as set forth in claim 12 wherein for the adjust the one or more of the plurality of therapeutic techniques of the treatment plan the processor is further configured to be capable of executing the stored programmed instructions to:

identify any stimming from the movement data;

wherein the adjust the one or more of the plurality of therapeutic techniques of the treatment plan is further based on any of the identified stimming from the movement data.

14. The apparatus as set forth in claim 11 wherein for the obtain analytic data and at least one of biomarker data from at least one biomarker sensor or environmental data the processor is further configured to be capable of executing the stored programmed instructions to:

obtain from at least one caregiver device observational data from monitoring the client during the execution of at least one of the therapeutic techniques;

wherein the adjust the one or more of the plurality of therapeutic techniques of the treatment plan is further based on the obtained observational data.

15. The apparatus as set forth in claim 11 wherein the biomarker data comprises one or more of heart rate, respiration, body temperature or anxiety level and wherein the environmental data comprises one or more of a temperature reading, a pressure reading, or lighting level reading.

16. The apparatus as set forth in claim 11 wherein for the adjust the one or more of the plurality of therapeutic techniques the processor is further configured to be capable of executing the stored programmed instructions to:

add an instruction that is configured to adjust at least one actuator coupled to control a device associated with the client.

17. The apparatus as set forth in claim 16 wherein the instruction further comprises a pressure adjustment instruction that is configured to adjust a pressure actuator coupled to control a pressure device associated with the client.

18. The apparatus as set forth in claim 16 wherein for the obtain analytic data and at least one of biomarker data from at least one biomarker sensor or environmental data the processor is further configured to be capable of executing the stored programmed instructions to:

obtain a current location of the client from at least one of the client device or the practitioner device;

wherein the instruction further comprises an environmental characteristic instruction that is configured to adjust an environmental actuator that is coupled to control an environmental characteristic device in a surrounding area associated with the client based on the obtained current location.

19. The apparatus as set forth in claim 11 wherein the processor is further configured to be capable of executing the stored programmed instructions to:

determine when an intervention in the treatment plan is required based on the analytic data and at least one of the biomarker data or the environmental data; and transmit in real time an electronic notice signaling the intervention to at least one of the practitioner device, a caregiver device, or the client device when the determination indicates the intervention is required.

20. The apparatus as set forth in claim 11 wherein for the transmit the adjusted one or more of the plurality of therapeutic techniques of the treatment plan the processor is further configured to be capable of executing the stored programmed instructions to:

determine which of the adjusted one or more of the plurality of therapeutic techniques of the treatment plan to be completed are to be carried out by the practitioner device or one of the at least one of the client device or a caregiver device; and transmit each of the adjusted one or more of the plurality of therapeutic techniques of the treatment plan to either the practitioner device or one of the at least one of the client device or the caregiver device based on the determination.

21. A non-transitory computer readable medium having stored thereon instructions comprising executable code which when executed by one or more processors, causes the one or more processors to:
generate a treatment plan comprising a plurality of therapeutic techniques that is transmitted to at least one of a client at a client device or a practitioner at a practitioner device associated with the client;
obtain analytic data regarding execution of at least one of the therapeutic techniques from at least one of the client device or the practitioner device, biomarker data from at least one biomarker sensor coupled to the client, environmental data from at least one environmental characteristic sensor, and environmental audiovisual data at a location of and external from the client during execution of the at least one of the therapeutic techniques;
adjust one or more of the plurality of therapeutic techniques of the treatment plan based on the obtained analytic data, the biomarker data, the environmental data, and environmental audiovisual data at the location of and external from the client, wherein the adjust the one or more of the plurality of therapeutic techniques of the treatment plan is further based on any threshold based changes in the environmental audiovisual data from any prior location of execution of the one or more therapeutic techniques for the client, wherein the adjust further comprises:
employing artificial intelligence to analyze the obtained analytic data, biomarker data, and environmental data for the client, additional obtained analytic data, biomarker data, and environmental data of one or more other clients correlated to the client based on a corresponding one of a plurality of types of conditions, and further additional obtained analytic data, biomarker data, and environmental data of one or more other additional clients having an uncorrelated one of the plurality of types of conditions to the client with two or more other correlated aspects to adjust the one or more of the plurality of therapeutic techniques of the treatment plan, wherein the two or more other correlated aspects comprise treatment plans, age, or social determinant data; and
transmit the adjusted one or more of the plurality of therapeutic techniques of the treatment plan to at least one of the client device or the practitioner device.

22. The medium as set forth in claim 21 wherein for the obtain analytic data and at least one of biomarker data from at least one biomarker sensor or environmental data the executable code when executed by the one or more processors further causes the one or more processors to:
obtain at least movement data from at least one movement sensor monitoring the client during the execution of at least one of the therapeutic techniques;
wherein the adjust the one or more of the plurality of therapeutic techniques of the treatment plan is further based on the obtained movement data.

23. The medium as set forth in claim 22 wherein for the adjust the one or more of the plurality of therapeutic techniques of the treatment plan the executable code when executed by the one or more processors further causes the one or more processors to:
identify any stimming from the movement data;
wherein the adjust the one or more of the plurality of therapeutic techniques of the treatment plan is further based on any of the identified stimming from the movement data.

24. The medium as set forth in claim 21 wherein for the obtain analytic data and at least one of biomarker data from at least one biomarker sensor or environmental data the executable code when executed by the one or more processors further causes the one or more processors to:
obtain from at least one caregiver device observational data from monitoring the client during the execution of at least one of the therapeutic techniques;
wherein the adjust the one or more of the plurality of therapeutic techniques of the treatment plan is further based on the obtained observational data.

25. The medium as set forth in claim 21 wherein the biomarker data comprises one or more of heart rate, respiration, body temperature or anxiety level and wherein the environmental data comprises one or more of a temperature reading, a pressure reading, or lighting level reading.

26. The medium as set forth in claim 21 wherein for the adjust the one or more of the plurality of therapeutic techniques the executable code when executed by the one or more processors further causes the one or more processors to:
add an instruction that is configured to adjust at least one actuator coupled to control a device associated with the client.

27. The medium as set forth in claim 26 wherein the instruction further comprises a pressure adjustment instruction that is configured to adjust a pressure actuator coupled to control a pressure device associated with the client.

28. The medium as set forth in claim 26 wherein for the obtain analytic data and at least one of biomarker data from at least one biomarker sensor or environmental data the executable code when executed by the one or more processors further causes the one or more processors to:
obtain a current location of the client from at least one of the client device or the practitioner device;
wherein the instruction further comprises an environmental characteristic instruction that is configured to adjust an environmental actuator that is coupled to control an environmental characteristic device in a surrounding area associated with the client based on the obtained current location.

29. The medium as set forth in claim 21 wherein the executable code when executed by the one or more processors further causes the one or more processors to:
determine when an intervention in the treatment plan is required based on the analytic data and at least one of the biomarker data or the environmental data; and
transmit in real time an electronic notice signaling the intervention to at least one of the practitioner device, a caregiver device, or the client device when the determination indicates the intervention is required.

30. The medium as set forth in claim 21 wherein for the transmit the adjusted one or more of the plurality of therapeutic techniques of the treatment plan the executable code when executed by the one or more processors further causes the one or more processors to:
determine which of the adjusted one or more of the plurality of therapeutic techniques of the treatment plan to be completed are to be carried out by the practitioner device or one of the at least one of the client device or a caregiver device; and
transmit each of the adjusted one or more of the plurality of therapeutic techniques of the treatment plan to either the practitioner device or one of the at least one of the client device or the caregiver device based on the determination.

* * * * *